(12) United States Patent
Chen et al.

(10) Patent No.: US 10,772,671 B2
(45) Date of Patent: *Sep. 15, 2020

(54) SYSTEM AND METHOD FOR TREATING CANCER THROUGH DNA DAMAGE WITH COLD ATMOSPHERIC PLASMA WITH SELF-ORGANIZED PATTERNS

(71) Applicant: US Patent Innovations, LLC, Takoma Park, MD (US)

(72) Inventors: Zhitong Chen, Ashburn, VA (US); Jerome Canady, Lakeland, FL (US); Michael Keidar, Baltimore, MD (US)

(73) Assignee: US Patent Innovations, LLC, Takoma Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/393,400

(22) Filed: Apr. 24, 2019

(65) Prior Publication Data

US 2019/0274747 A1 Sep. 12, 2019

Related U.S. Application Data

(63) Continuation-in-part of application No. 16/298,484, filed on Mar. 11, 2019.

(Continued)

(51) Int. Cl.
*A61B 18/04* (2006.01)
*A61B 17/00* (2006.01)
*A61B 18/00* (2006.01)

(52) U.S. Cl.
CPC .. *A61B 18/042* (2013.01); *A61B 2017/00526* (2013.01); *A61B 2018/00333* (2013.01)

(58) Field of Classification Search
CPC ........ A61B 18/042; A61B 2018/00333; A61B 2017/00526; A61K 41/00
See application file for complete search history.

(56) References Cited

U.S. PATENT DOCUMENTS

| 9,999,462 B2 | 6/2018 | Canady et al. |
| 10,213,614 B2 | 2/2019 | Keidar et al. |

FOREIGN PATENT DOCUMENTS

WO 2018191265 A1 10/2018

OTHER PUBLICATIONS

Chen et al. ("In vitro Demonstration of Cancer Inhibiting Properties from Straitified Self-Organized MicroDischarge Plasma-Liquid Interface" pp. I-17, 2017), Sep. 22, 2017.*

(Continued)

*Primary Examiner* — Blessing M Fubara
(74) *Attorney, Agent, or Firm* — 24IP Law Group USA, PLLC; Timothy Dewitt

(57) ABSTRACT

Cold atmospheric plasma is an emerging technology in the treatment of cancer. Meanwhile, different types of self-organized pattern (SOP) phenomenon have been reported in a wide of range of plasmas. In this paper, we describe the application of SOP plasma to two breast cancer cells MDA-MB-231 and MCF-7. Specifically, the effect of SOP plasma on reactive oxygen and nitrogen species (RONS) were investigated. SOP plasma-generated RONS displayed significantly decreased cancer cell viability in both breast cancer cell lines; significantly inhibiting cell proliferation via while inducing apoptosis. SOP plasma induced DNA damage, activating the ATM/ATR kinase signaling cascade. ATR phosphorylates the checkpoint effector kinase Chk-1 activating γ-H2AX resulting in cell cycle arrest and ATM induced apoptosis. Taken together, we have provided new insight into the action mechanism of action by which elevated SOP plasma first induces ROS generation and then results into a DNA damage response, ultimately inducing apoptosis.

12 Claims, 12 Drawing Sheets

Related U.S. Application Data

(60) Provisional application No. 62/662,466, filed on Apr. 25, 2018, provisional application No. 62/640,886, filed on Mar. 9, 2018.

(56) References Cited

OTHER PUBLICATIONS

Preliminary Amendment filed May 1, 2020.*
C.E. DeSantis, J. Ma, A. Goding Sauer, L.A. Newman, A. Jemal, Breast cancer statistics, 2017, racial disparity in mortality by state, CA: a cancer journal for clinicians 67(6) (2017) 439-448.
A. Jemal, R. Siegel, J. Xu, E. Ward, Cancer statistics, 2010, CA: a cancer journal for clinicians 60(5) (2010) 277-300.
L. Hutchinson, Breast cancer: Challenges, controversies, breakthroughs, Nature Reviews Clinical Oncology 7 (2010) 669-670.
G. Fridman, G. Friedman, A. Gutsol, A.B. Shekhter, V.N. Vasilets, A. Fridman, Applied plasma medicine, Plasma Processes and Polymers 5(6) (2008) 503-533.
M. Keidar, Plasma for cancer treatment, Plasma Sources Science and Technology 24(3) (2015) 033001.
M. Keidar, A. Shashurin, O. Volotskova, M. Ann Stepp, P. Srinivasan, A. Sandler, B. Trink, Cold atmospheric plasma in cancer therapy, Physics of PLasmas 20(5) (2013) 057101.
E. Stoffels, Y. Sakiyama, D.B. Graves, Cold atmospheric plasma: charged species and their interactions with cells and tissues, IEEE Transactions on Plasma Science 36(4) (2008) 1441-1457.
S.B. Karki, T.T. Gupta, E. Yildirim-Ayan, K.M. Eisenmann, H. Ayan, Investigation of non-thermal plasma effects on lung cancer cells within 3D collagen matrices, Journal of Physics D: Applied Physics 50(31) (2017) 315401.
S.B. Karki, E. Yildirim-Ayan, K.M. Eisenmann, H. Ayan, Miniature dielectric barrier discharge nonthermal plasma induces apoptosis in lung cancer cells and inhibits cell migration, BioMed research international 2017 (2017).
Yan, D.; Sherman, J. H.; Cheng, X.; Ratovitski, E.; Canady, J.; Keidar, M. Controlling plasma stimulated media in cancer treatment application. Appl. Phys. Lett. 2014, 105, 224101.
Z. Chen, H. Simonyan, X. Cheng, E. Gjika, L. Lin, J. Canady, J.H. Sherman, C. Young, M. Keidar, A novel micro cold atmospheric plasma device for glioblastoma both in vitro and in vivo, Cancers 9(6) (2017) 61.
O. Volotskova, T.S. Hawley, M.A. Stepp, M. Keidar, Targeting the cancer cell cycle by cold atmospheric plasma, Scientific reports 2 (2012) 636.
P. Attri, T. Sarinont, M. Kim, T. Amano, K. Koga, A.E. Cho, E.H. Choi, M. Shiratani, Influence of ionic liquid and ionic salt on protein against the reactive species generated using dielectric barrier discharge plasma, Scientific reports 5 (2015) 17781.
Z. Chen, L. Lin, X. Cheng, E. Gjika, M. Keidar, Treatment of gastric cancer cells with nonthermal atmospheric plasma generated in water, Biointerphases 11(3) (2016) 031010.
A. Shashurin, M. Keidar, S. Bronnikov, R. Jurjus, M. Stepp, Living tissue under treatment of cold plasma atmospheric jet, Applied Physics Letters 93(18) (2008) 181501.
S.N. Zucker, J. Zirnheld, A. Bagati, T.M. DiSanto, B. Des Soye, J.A. Wawrzyniak, K. Etemadi, M. Nikiforov, R. Berezney, Preferential induction of apoptotic cell death in melanoma cells as compared with normal keratinocytes using a non-thermal plasma torch, Cancer biology & therapy 13(13) (2012) 1299-1306.
Z. Chen, L. Lin, E. Gjika, X. Cheng, J. Canady, M. Keidar, Selective treatment of pancreatic cancer cells by plasma-activated saline solutions, IEEE Transactions on Radiation and Plasma Medical Sciences (2017).
Z. Chen, S. Zhang, I. Levchenko, I.I. Beilis, M. Keidar, In vitro Demonstration of Cancer Inhibiting Properties from Stratified Self-Organized Plasma-Liquid Interface, Scientific reports 7(1) (2017) 12163.
Radehaus C. Dirksmeyer, T., Willebrand, H. & Purwins, H.-G. Pattern formation in gas discharge systems with high impedance electrodes. Physics Letters A 125, 92-94 (1987).
Jäger, D., Baumann, H. & Symanczyk, R. Experimental observation of spatial structures due to current filament formation in silicon pin diodes. Physics Letters A 117, 141-144 (1986).
Raizer, Y. P. & Mokrov, M. Physical mechanisms of self-organization and formation of current patterns in gas discharges of the Townsend and glow types. Physics of Plasmas 20, 101604 (2013).
Trelles, J. P. Formation of self-organized anode patterns in arc discharge simulations. Plasma Sources Science and Technology 22, 025017 (2013).
Kogelschatz, U. Filamentary, patterned, and diffuse barrier discharges. IEEE Transactions on plasma science 30, 1400-1408 (2002).
Shi, J., Liu, D. & Kong, M. G. Plasma stability control using dielectric barriers in radio-frequency atmospheric pressure glow discharges. Applied physics letters 89, 081502 (2006).
Akishev, Y. et al. The influence of electrode geometry and gas flow on corona-to-glow and glow-to-spark threshold currents in air. Journal of Physics D: Applied Physics 34, 2875 (2001).
Shirai, N., Ibuka, S. & Ishii, S. Atmospheric DC glow discharge observed in intersecting miniature gas flows. IEEE Transactions on Plasma Science 36, 960-961 (2008).
Laroussi, M., Alexeff, I., Richardson, J. P. & Dyer, F. F. The resistive barrier discharge. IEEE Transactions on Plasma Science 30, 158-159 (2002).
Laroussi, M., Lu, X. & Malott, C. M. A non-equilibrium diffuse discharge in atmospheric pressure air. Plasma Sources Science and Technology 12, 53 (2003).
André, P. et al. Experimental study of discharge with liquid non-metallic (tap-water) electrodes in air at atmospheric pressure. Journal of Physics D: Applied Physics 34, 3456 (2001).
Chen, Z., Zhang, S., Levchenko, I., Beilis, I. I. & Keidar, M. In vitro Demonstration of Cancer Inhibiting Properties from Stratified Self-Organized Micro-Discharge Plasma-Liquid Interface. arXiv preprint arXiv:1701.01655 (2017).
Benilov, M. Bifurcations of current transfer through a collisional sheath with ionization and selforganization on glow cathodes. Physical Review E 77, 036408 (2008).
Schoenbach, K. H., Moselhy, M. & Shi, W. Self-organization in cathode boundary layer microdischarges. Plasma Sources Science and Technology 13, 177 (2004).
Dong, L., Fan, W., He, Y. & Liu, F. Self-organized gas-discharge patterns in a dielectric-barrier discharge system. IEEE Transactions on Plasma Science 36, 1356-1357 (2008).
Dong, L. et al. Collective vibration of discharge current filaments in a self-organized pattern within a dielectric barrier discharge. Physical Review E 85, 066403 (2012).
Shirai, N., Uchida, S. & Tochikubo, F. Influence of oxygen gas on characteristics of self-organized luminous pattern formation observed in an atmospheric dc glow discharge using a liquid electrode. Plasma Sources Science and Technology 23, 054010 (2014).
Shirai, N., Ibuka, S. & Ishii, S. Self-organization pattern in the anode spot of an atmospheric glow microdischarge using an electrolyte anode and axial miniature helium flow. Applied Physics Express 2, 036001 (2009).
Zheng, P. et al. Selforganized pattern formation of an atmospheric-pressure, ac glow discharge with an electrolyte electrode. Plasma Sources Science and Technology 24, 015010 (2014).
Locke, B., Sato, M., Sunka, P., Hoffmann, M. & Chang, J.-S. Electrohydraulic discharge and nonthermal plasma for water treatment. Industrial & engineering chemistry research 45, 882-905 (2006).
Ostrikov, K. K., Cvelbar, U. & Murphy, A. B. Plasma nanoscience: setting directions, tackling grand challenges. Journal of Physics D: Applied Physics 44, 174001 (2011).
Richmonds, C. & Sankaran, R. M. Plasma-liquid electrochemistry: rapid synthesis of colloidal metal nanoparticles by microplasma reduction of aqueous cations. Applied Physics Letters 93, 131501 (2008).

(56) References Cited

OTHER PUBLICATIONS

Kong, M. G. et al. Plasma medicine: an introductory review. new Journal of Physics 11, 115012 (2009).

* cited by examiner

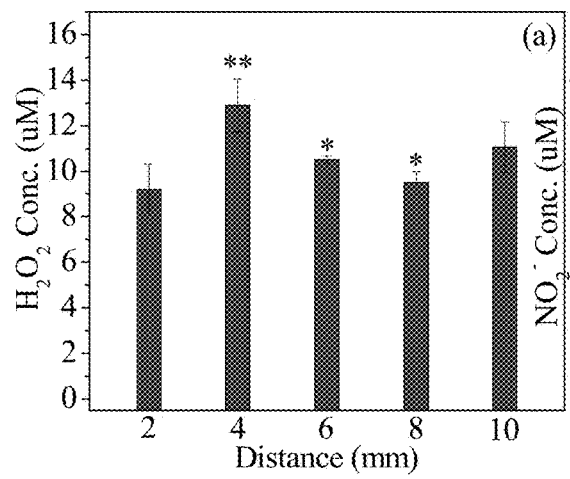
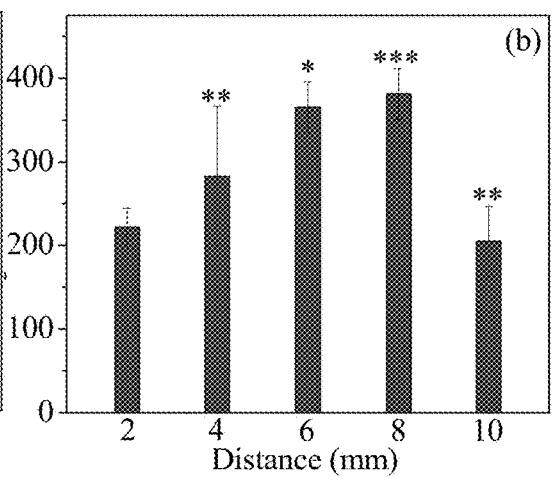
FIG. 4A
FIG. 4B
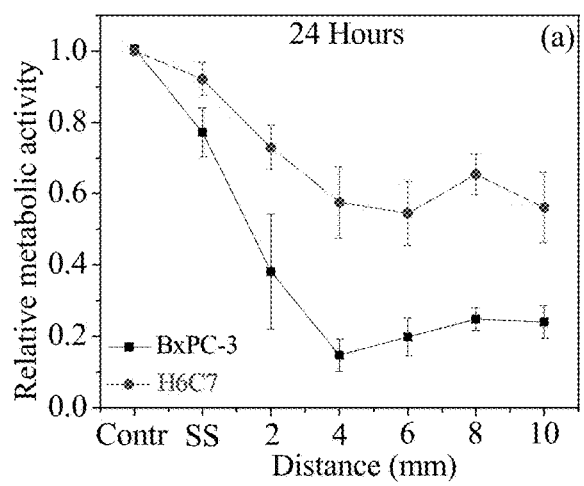
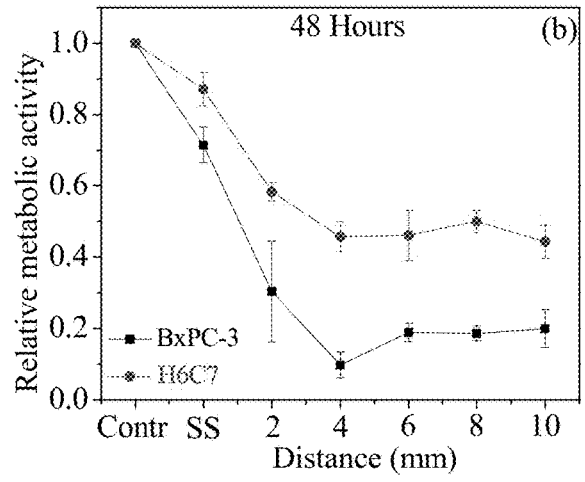
FIG. 5A
FIG. 5B

SYSTEM AND METHOD FOR TREATING CANCER THROUGH DNA DAMAGE WITH COLD ATMOSPHERIC PLASMA WITH SELF-ORGANIZED PATTERNS

CROSS-REFERENCE TO RELATED APPLICATIONS

The present application claims the benefit of the filing date of U.S. Provisional Patent Application Ser. No. 62/662,466 filed by the present inventors on Apr. 25, 2018 and is a continuation-in-part of U.S. patent application Ser. No. 16/298,484 filed on Mar. 11, 2019, which claims the benefit of U.S. Provisional Patent Application Ser. No. 62/640,886 filed on Mar. 9, 2018.

The aforementioned patent applications are hereby incorporated by reference in their entirety.

STATEMENT REGARDING FEDERALLY SPONSORED RESEARCH OR DEVELOPMENT

None.

BACKGROUND OF THE INVENTION

Field of the Invention

The present invention relates to systems and methods for using Cold Atmospheric Plasma ("CAP") to treat cancer.

Brief Description of the Related Art

Breast cancer is one of the most common cancers diagnosed among American women (excluding skin cancers), which is the second leading cause of cancer death among women after lung cancer. See, C. E. DeSantis, J. Ma, A. Goding Sauer, L. A. Newman, A. Jemal, Breast cancer statistics, 2017, racial disparity in mortality by state, CA: a cancer journal for clinicians 67(6) (2017) 439-448. The global burden of breast cancer exceeds all other cancers and the incidence rates of breast cancer are increasing. A. Jemal, R. Siegel, J. Xu, E. Ward, Cancer statistics, 2010, CA: a cancer journal for clinicians 60(5) (2010) 277-300. Different treatment methods including surgical techniques, medication drugs, and radiation-based approaches are routinely being used for breast cancer. L. Hutchinson, Breast cancer: Challenges, controversies, breakthroughs, Nature Reviews Clinical Oncology 7 (2010) 669-670. However, additional treatment modalities need to be developed to minimize the morbidity and mortality associated with this disease. Breast cancer represent a multitude of different diseases with intratumoral and intertumoral genetic and epigenetic alterations.

Plasma medicine is emerging as an innovative field for cancer therapy, which combines biology, chemistry, plasma, and medicine. See, G. Fridman, G. Friedman, A. Gutsol, A. B. Shekhter, V. N. Vasilets, A. Fridman, Applied plasma medicine, Plasma Processes and Polymers 5(6) (2008) 503-533 and M. Keidar, Plasma for cancer treatment, Plasma Sources Science and Technology 24(3) (2015) 033001. Plasma is one of the four fundamental states of matter, and is a fully or partially ionized gas. See, M. Keidar, A. Shashurin, O. Volotskova, M. Ann Stepp, P. Srinivasan, A. Sandler, B. Trink, Cold atmospheric plasma in cancer therapy, Physics of Plasmas 20(5) (2013) 057101. Historically, plasma could be generated only at high temperatures or in vacuum, while more recent studies have reported on plasma generated at atmospheric pressure and at room temperature (cold atmospheric plasma, CAP). See, E. Stoffels, Y. Sakiyama, D. B. Graves, Cold atmospheric plasma: charged species and their interactions with cells and tissues, IEEE Transactions on Plasma Science 36(4) (2008) 1441-1457; S. B. Karki, T. T. Gupta, E. Yildirim-Ayan, K. M. Eisenmann, H. Ayan, Investigation of non-thermal plasma effects on lung cancer cells within 3D collagen matrices, Journal of Physics D: Applied Physics 50(31) (2017) 315401; and S. B. Karki, E. Yildirim-Ayan, K. M. Eisenmann, H. Ayan, Miniature dielectric barrier discharge non-thermal plasma induces apoptosis in lung cancer cells and inhibits cell migration, BioMed research international 2017 (2017).

CAP has attracted a lot of attentions because of its remarkable potential to affect biological processes. Yan, D.; Sherman, J. H.; Cheng, X.; Ratovitski, E.; Canady, J.; Keidar, M. Controlling plasma stimulated media in cancer treatment application. Appl. Phys. Lett. 2014, 105, 224101. The potential of CAP in diverse bio-medical applications has been explored, including wound treatments, blood coagulation, disinfection, control of inflammation, regenerative medicine, and cancer therapy. Z. Chen, H. Simonyan, X. Cheng, E. Gjika, L. Lin, J. Canady, J. H. Sherman, C. Young, M. Keidar, A novel micro cold atmospheric plasma device for glioblastoma both in vitro and in vivo, Cancers 9(6) (2017) 61. The efficacy of CAP in the proposed applications relies on the synergistic action of the reactive oxygen species (ROS), reactive nitrogen species (RNS), free radicals, ultra-violet (UV) photons, charged particles, and electric fields. See, S. B. Karki, T. T. Gupta, E. Yildirim-Ayan, K. M. Eisenmann, H. Ayan, Investigation of non-thermal plasma effects on lung cancer cells within 3D collagen matrices, Journal of Physics D: Applied Physics 50(31) (2017) 315401 and O. Volotskova, T. S. Hawley, M. A. Stepp, M. Keidar, Targeting the cancer cell cycle by cold atmospheric plasma, Scientific reports 2 (2012) 636.

ROS and RNS, combined or independently, are known to promote cell proliferation as well as cell death, additionally, extreme amounts of ROS and RNS may lead to the damage of proteins, lipids, senescence and induce apoptosis. P. Attri, T. Sarinont, M. Kim, T. Amano, K. Koga, A. E. Cho, E. H. Choi, M. Shiratani, Influence of ionic liquid and ionic salt on protein against the reactive species generated using dielectric barrier discharge plasma, Scientific reports 5 (2015) 17781 and Z. Chen, L. Lin, X. Cheng, E. Gjika, M. Keidar, Treatment of gastric cancer cells with nonthermal atmospheric plasma generated in water, Biointerphases 11(3) (2016) 031010. Many studies of CAP for cancer treatment have shown that CAP dose not harm normal tissues when applied at the appropriate dosages. See, A. Shashurin, M. Keidar, S. Bronnikov, R. Jurjus, M. Stepp, Living tissue under treatment of cold plasma atmospheric jet, Applied Physics Letters 93(18) (2008) 181501 and S. N. Zucker, J. Zirnheld, A. Bagati, T. M. DiSanto, B. Des Soye, J. A. Wawrzyniak, K. Etemadi, M. Nikiforov, R. Berezney, Preferential induction of apoptotic cell death in melanoma cells as compared with normal keratinocytes using a non-thermal plasma torch, Cancer biology & therapy 13(13) (2012) 1299-1306. Taken together, CAP therapy has been introduced as a cost effective, rapid and selective treatment modality for killing cancer cells. In addition, CAP with self-organized patterns has recently attracted significant attentions on cancer therapy. Z. Chen, L. Lin, E. Gjika, X. Cheng, J. Canady, M. Keidar, Selective treatment of pancreatic cancer cells by plasma-activated saline solutions, IEEE Transactions on Radiation and Plasma Medical Sciences (2017) and Z. Chen, S. Zhang, I. Levchenko, I. I. Beilis, M. Keidar, In vitro Demonstration of Cancer Inhibiting Properties from Stratified Self-Organized Plasma-Liquid Interface, Scientific reports 7(1) (2017) 12163.

Self-organization is generally referred to as a process of spontaneous transition from a homogeneous stable state to a regular pattern in a spatially extended system. See, Radehaus, C., Dirksmeyer, T., Willebrand, H. & Purwins, H.-G. Pattern formation in gas discharge systems with high impedance electrodes. *Physics Letters A* 125, 92-94 (1987) and Jäger, D., Baumann, H. & Symanczyk, R. Experimental observation of spatial structures due to current filament formation in silicon pin diodes. *Physics Letters A* 117, 141-144 (1986). Self-organization is a complex and fascinating phenomenon commonly observed in both natural and technological contexts within diverse varieties of physics, chemistry and biology. Raizer, Y. P. & Mokrov, M. Physical mechanisms of self-organization and formation of current patterns in gas discharges of the Townsend and glow types. *Physics of Plasmas* 20, 101604 (2013) and Trelles, J. P. Formation of self-organized anode patterns in arc discharge simulations. *Plasma Sources Science and Technology* 22, 025017 (2013). Different types of self-organization phenomena have been reported in a wide range of plasmas, such as dielectric barrier discharge (see, Kogelschatz, U. Filamentary, patterned, and diffuse barrier discharges. *IEEE Transactions on plasma science* 30, 1400-1408 (2002)), high frequency discharge (see, Shi, J., Liu, D. & Kong, M. G. Plasma stability control using dielectric barriers in radiofrequency atmospheric pressure glow discharges. *Applied physics letters* 89, 081502 (2006)), gas flow stabilized discharges (see, Akishev, Y. et al. The influence of electrode geometry and gas flow on corona-to-glow and glow-to-spark threshold currents in air. *Journal of Physics D: Applied Physics* 34, 2875 (2001) and Shirai, N., Ibuka, S. & Ishii, S. Atmospheric DC glow discharge observed in intersecting miniature gas flows. *IEEE Transactions on Plasma Science* 36, 960-961 (2008)), resistively stabilized discharged (see, Laroussi, M., Alexeff, I., Richardson, J. P. & Dyer, F. F. The resistive barrier discharge. *IEEE Transactions on Plasma Science* 30, 158-159 (2002)), and discharges with liquid electrodes (see, Laroussi, M., Lu, X. & Malott, C. M. A non-equilibrium diffuse discharge in atmospheric pressure air. *Plasma Sources Science and Technology* 12, 53 (2003), André, P. et al. Experimental study of discharge with liquid non-metallic (tap-water) electrodes in air at atmospheric pressure. *Journal of Physics D: Applied Physics* 34, 3456 (2001) and Chen, Z., Zhang, S., Levchenko, I., Beilis, I. I. & Keidar, M. In vitro Demonstration of Cancer Inhibiting Properties from Stratified Self-Organized Micro-Discharge Plasma-Liquid Interface. arXiv preprint arXiv:1701.01655 (2017)). The self-organization phenomena associated with the formation of electrode patterns are significantly different among these discharges, which typically occur in the anode or cathode layer. Benilov, M. Bifurcations of current transfer through a collisional sheath with ionization and self-organization on glow cathodes. *Physical Review E* 77, 036408 (2008) and Schoenbach, K. H., Moselhy, M. & Shi, W. Self-organization in cathode boundary layer microdischarges. *Plasma Sources Science and Technology* 13, 177 (2004). Self-organization patterns (SOPs) of plasma include square-textures, square-lattices, square/hexagonal superlattices, hollow-hexagonal, multi-armed spirals, rotating-wheels patterns, etc. Dong, L., Fan, W., He, Y. & Liu, F. Self-organized gas-discharge patterns in a dielectric-barrier discharge system. *IEEE Transactions on Plasma Science* 36, 1356-1357 (2008) and Dong, L. et al. Collective vibration of discharge current filaments in a self-organized pattern within a dielectric barrier discharge. *Physical Review E* 85, 066403 (2012). The formation of these patterns depends on various parameters such as driving current, electrolyte conductivity, gap length, gas species, and so on. See, Shirai, N., Uchida, S. & Tochikubo, F. Influence of oxygen gas on characteristics of self-organized luminous pattern formation observed in an atmospheric dc glow discharge using a liquid electrode. *Plasma Sources Science and Technology* 23, 054010 (2014), Shirai, N., Ibuka, S. & Ishii, S. Self-organization pattern in the anode spot of an atmospheric glow microdischarge using an electrolyte anode and axial miniature helium flow. *Applied Physics Express* 2, 036001 (2009) and Zheng, P. et al. Self-organized pattern formation of an atmospheric-pressure, ac glow discharge with an electrolyte electrode. *Plasma Sources Science and Technology* 24, 015010 (2014). Recently, plasma discharges with the liquid electrode have been studied referring to applications ranging from water decontamination and activation (see, Locke, B., Sato, M., Sunka, P., Hoffmann, M. & Chang, J.-S. Electrohydraulic discharge and nonthermal plasma for water treatment. *Industrial & engineering chemistry research* 45, 882-905 (2006) and Ostrikov, K. K., Cvelbar, U. & Murphy, A. B. Plasma nanoscience: setting directions, tackling grand challenges. *Journal of Physics D: Applied Physics* 44, 174001 (2011)), to nanoparticle and materials synthesis (Ostrikov, K. K., Cvelbar, U. & Murphy, A. B. Plasma nanoscience: setting directions, tackling grand challenges. *Journal of Physics D: Applied Physics* 44, 174001 (2011) and Richmonds, C. & Sankaran, R. M. Plasma-liquid electrochemistry: rapid synthesis of colloidal metal nanoparticles by microplasma reduction of aqueous cations. *Applied Physics Letters* 93, 131501 (2008)), and medicine (see, Kong, M. G. et al. Plasma medicine: an introductory review. *new Journal of Physics* 11, 115012 (2009)). Therefore, self-organization in plasma interacting with surfaces is interest not only from a fundamental point of view as intrinsic and fascinating characteristics of nature, but also from practical standpoint in current and emerging technological applications.

SUMMARY OF THE INVENTION

The present invention creates plasma with different self-organization patterns (SOPs) to activate saline solution. The plasma activated saline solutions have anti-tumor effects on human cancer cells.

Plasma interacting with the liquid generates reactive oxygen species (ROS) and reactive nitrogen species (RNS) that act as key intermediate for cancer therapy. See, Boehm, D., Heslin, C., Cullen, P. J. & Bourke, P. Cytotoxic and mutagenic potential of solutions exposed to cold atmospheric plasma. *Scientific reports* 6 (2016); Chen, Z. et al. A Novel Micro Cold Atmospheric Plasma Device for Glioblastoma Both In Vitro and In Vivo. *Cancers* 9, 61 (2017). The present invention creates plasma with different self-organization patterns (SOPs) to activate a media such as saline solution. The plasma activated medias have anti-tumor effects on human normal and cancer cells. A camera was used to characterize the patterns of plasma with SOP. The spectra of plasma with SOPs were determined by UV-visible-NIR optical emission spectroscopy OES). The concentration of hydrogen peroxide ($H_2O_2$) and nitrite ($NO_2^-$) was measured by using a Fluorimetric hydrogen peroxide assay kit, and the Griess reagent system, respectively. The cell viability of H6c7 and BxPC-3 was measured via Cell Counting KIT 8 Assay. Typically, saline solution is used to treat dehydration by injection into a vein, and it is also used to dilute medications to be given by injection. Based on the results, one can suggest that SOP plasma-activated saline solutions (plasma solutions) has the potential to be utilized as an oral medicine or drug injected into tumors.

In a preferred embodiment, the present invention is a method for manufacturing plasma-activated media for treatment of cancer cells. The method comprises immersing a first electrode in a media in a container, positioning a second electrode at a fixed distance from a surface of the media in the container, and applying electrical energy to the second electrode for a fixed period of time, wherein the fixed distance and the fixed period of time are selected to cause a plasma self-organized pattern at a surface of the media with an atmospheric discharge between the second electrode and the first electrode. The fixed distance preferably is 4-6 mm. The fixed time may be, for example, 40 seconds.

In another preferred embodiment, the present invention is a method for treatment of cancer cells. The method comprises positioning an electrode at a distance of less than 10 mm from a surface of a media in a container, flowing an inert gas past the electrode and onto the surface of the media in the container, applying electrical energy to the electrode while the inert gas is flowing past the electrode for a fixed period of time to create a plasma self-organized pattern at a surface of the media to induce ROS generation in the media, and exposing human cancer cells to the plasma activated media to cause DNA damage in the human cancer cells. The step of treating human cancer cells with the 9101-078 plasma activated media may comprise injecting the plasma activated media into an area of a human body containing the human cancer cells. The human cancer cells comprise human breast cancer cells.

In yet another preferred embodiment, the present invention is a method for manufacturing plasma-activated media for treatment of cancer cells. The method comprises generating with an atmospheric discharge between an electrode and a surface of a liquid media to generate a plasma self-organized pattern at the surface of media, wherein the electrode is at a distance from the surface of the media and a plasma is formed in a gap between the electrode and the surface of the media, and maintaining the atmospheric discharge for a period of time greater than 10 seconds. The self-organized pattern may comprise a double ring.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 4A and 4B $H_2O_2$ and $NO_2^-$ concentrations in saline solution treated by plasma with self-organized pattern plasma with different air gap length (Each air gap length treated by SOP plasma for 40 seconds): (a) $H_2O_2$ concentration and (b) $NO_2^-$ concentration. Student's t-test was performed, and the significance compared to the 2 mm is indicated as *$p<0.05$, $p<0.01$, * $<0.001$. (n=3)

FIGS. 5A and 5B show effects of seven media: RPMI/KSFM, saline solution (SS), and five plasma-activated media (saline solution activated by plasma with SOP at 2, 4, 6, 8, and 10 mm distance for 40 seconds' treatment) on viability of the BxPC-3 human pancreas cancer cells and the H6c7 human pancreas normal cells after 24 (a) and 48 (b) hours' incubation, respectively. The percentages of surviving cells for each cell line were calculated relative to controls (RPMI/KSFM).

FIG. 7A shows typical comet images from both breast cancer cells treated with SOP plasma with 6V, 8V, 10V, and 12V input voltage, representing different levels of damage. (b) MDA-MB-231 and MCF-7 were treated by SOP plasma with 6V, 8V, 10V, and 12V input voltage, and then the expressions of CHK1-p137 and γ-H2AX were detected by western blotting. GAPDH was used as a loading control. (c) MDA-MB-23 land MCF-7 were infected by SOP plasma at 10V input voltage, and then γ-H2AX foci formation was determined by immunofluorescence staining.

DETAILED DESCRIPTION OF THE PREFERRED EMBODIMENTS

The preferred embodiments of the invention and the experiments will be described with reference to the drawings.

Figure 1:
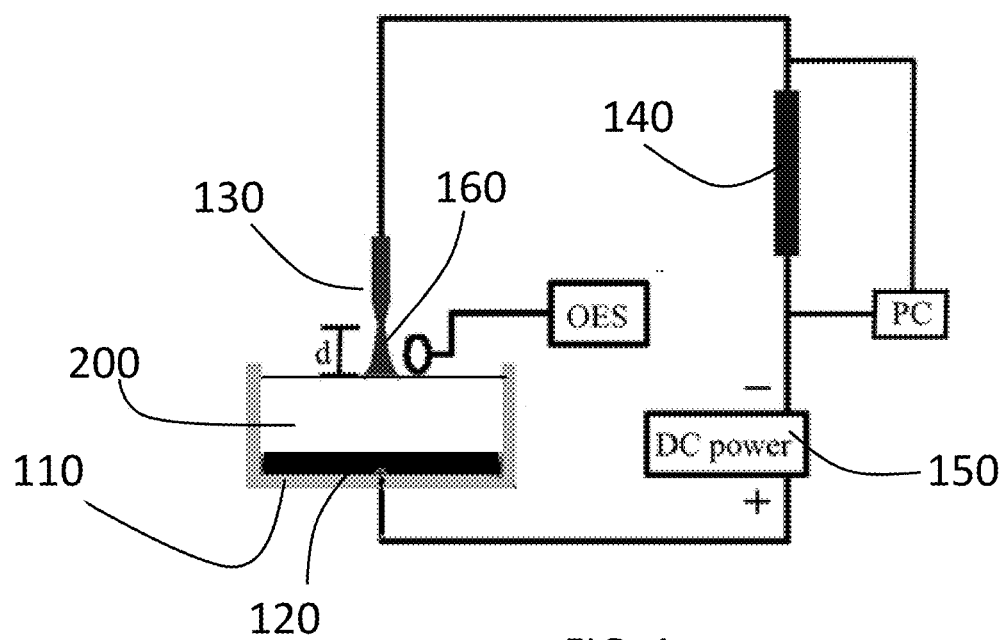
FIG. 1 shows a schematic representation of the SOP plasma discharge setup capable of producing well-defined self-organized interface patterns at the surface of the liquid/plasma interface. Different air gap distances between the cathode and surface of liquid accommodated plasma. (d is the distance of air gap).
Figure 2A:
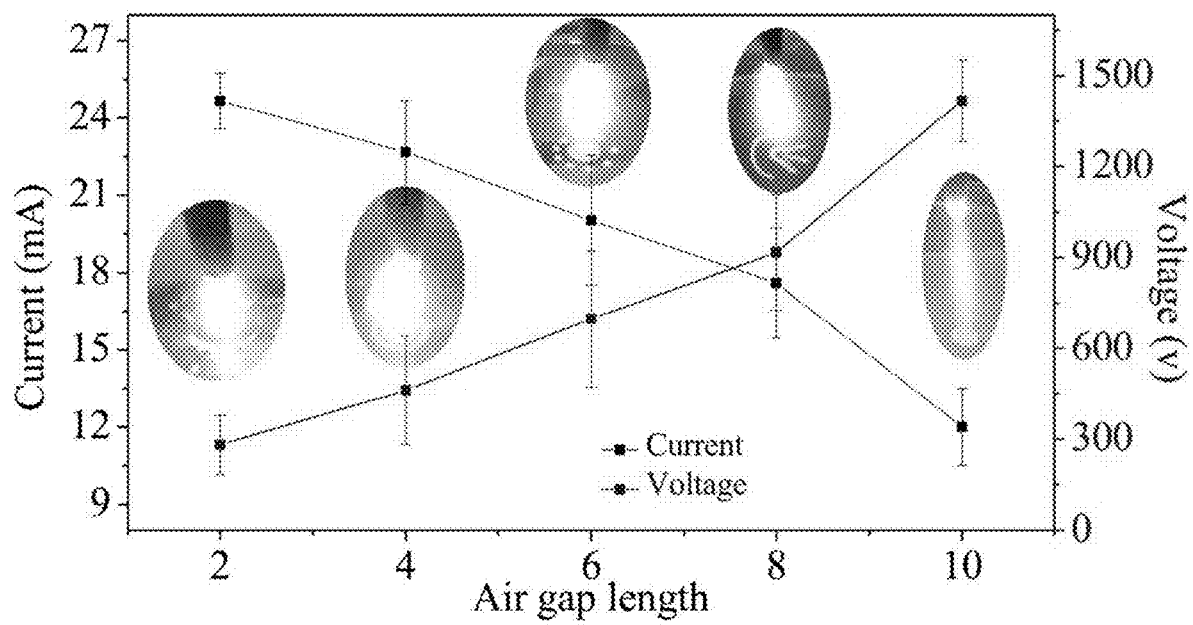
FIG. 2A illustrate a current-voltage dependence for different air gap lengths with optical photographs of the self-organized stratified interface patterns.

FIG. 1A shows a schematic representation of a self-organized pattern plasma discharge setup capable of producing well-defined self-organized interface patterns at the surface of a liquid/plasma interface. An anode 120 (a thin copper plate, thickness d=0.2 mm, Ø=22 mm) is placed at the bottom of a glass-made well 110. A saline solution 200 is placed in the glass well. A tungsten cathode 130 of Ø=2 mm is then installed above the saline solution surface. A ballast resistor 140 (90 kΩ) is connected between the cathode 130 and a direct current (DC) power supply unit 150 (Power Design, Model 1570A, 1-3012V, 40 mA). A voltage is applied between the cathode 130 and the liquid-immersed anode 120, and a plasma 160 is formed in a small (2-10 mm) gap between the cathode and liquid surface accommodated. As shown in FIG. 2A, voltage of 300-1500 v were applied with currents of approximately 10-25 mA.

In a series of experiments, saline solution was treated by discharge with a 2, 4, 6, 8, and 10 mm air gap length d between the cathode 130 and the surface of the plasma 200 to obtain plasma-activated solutions for treating cancer cells.

A. Cell Cultures for the Pancreatic Experiments

The human pancreas adenocarcinoma cancer cell line (BxPC-3) was acquired from American Type Culture Collection (ATCC). Cell lines were cultured in RPMI-1640 Medium (ATCC® 30-2001™) supplemented with 10% (v/v) fetal bovine serum (Atlantic Biologicals) and 1% (v/v) penicillin and streptomycin (Life Technologies). The human pancreatic duct epithelial normal cell line (H6c7, Kerafast) was cultured in Keratinocyte SFM (KSFM, Gibco) supplemented with prequalified human recombinant Epidermal Growth Factor 1-53 (EGF 1-53, Gibco), Bovine Pituitary Extract (BPE, Gibco), and 1% (v/v) penicillin and streptomycin (Life Technologies). Cultures were maintained at 37° C. in a humidified incubator containing 5% (v/v) $CO_2$. Cultures were maintained at 37° C. in a humidified incubator containing 5% (v/v) $CO_2$.

B. Evaluation of Hydrogen Peroxide ($H_2O_2$) Concentration

Fluorimetric Hydrogen Peroxide Assay Kit (Sigma-Aldrich) was used for measuring the amount of $H_2O_2$ in saline solution. A detailed protocol can be found on the Sigma-Aldrich website. Briefly, we added 50 μl of standard curves samples, controls, and experimental samples (saline solution treated by SOP plasma with 2, 4, 6, 8, and 10 mm air gap) to the 96-well flat-bottom black plates, and then added 50 μl of Master Mix (including Red Peroxidase Substrate Stock, 20 units/mL Peroxidase Stock, and Assay Buffer) to each of wells. We incubated the plates for 20 min at room temperature protected from light on and measured fluorescence by Synergy H1 Hybrid Multi-Mode Microplate Reader at Ex/Em: 540/590 nm.

C. Evaluation of Nitrite ($NO_2^-$) Concentration

Nitrite level were determined by using the Griess Reagent System, including 50 ml Sulfanilamide Solution, 50 ml NED solution, and 1 ml Nitrite Standard, (Promega Corporation) according to the instructions provided by the manufacturer. Briefly, we added 50 μl of standard curves samples, controls, and experimental samples to the 96-well flat-bottom plates. Then dispense 50 μl of the Sulfanilamide Solution to all samples and incubate 5-10 minutes at room temperature. Finally, dispense 50 μl of the NED solution to all wells and incubate at room temperature 5-10 minutes. The absorbance was measured at 540 nm by Synergy H1 Hybrid Multi-Mode Microplate Reader.

D. Measurement of Cell Viability

The cells were plated in 96-well flat-bottom microplates at a density of 3000 cells per well in 70 μL of complete culture medium. Cells were incubated for 24 hours to ensure proper cell adherence and stability. Confluence of each well was confirmed to be at ~40%. 30 μl of RPMI, saline solution, and plasma-activated saline solutions were added to the corresponding cells. Cells were further incubated at 37° C. for 24 and 48 hours. The viability of the pancreas normal and cancer cells was measured with Cell Counting Kit 8 assay (Dojindo Molecular Technologies, MD). The original culture medium was aspirated and 10 μL of CCK 8 reagent was added per well. The plates were incubated for 3 hours at 37° C. The absorbance was measured at 450 nm by Synergy H1 Hybrid Multi-Mode Microplate Reader. We normalized data according to control group (RPMI for BxPC-3, and KSFM for H6c7). We calculated the mean and standard deviation independently.

E. Optical Emission Spectra Measurement

UV-visible-NIR, a range of wavelength 200-850 nm, was investigated on plasma to detect various RNS and ROS (nitrogen [$N_2$], nitric oxide [—NO], nitrogen cation [$N^{+2}$], atomic oxygen [O], and hydroxyl radical [—OH]). The spectrometer and the detection probe were purchased from Stellar Net Inc. The optical probe was placed 2 cm in front of the plasma beam. Integration time of the collecting data was set to 100 ms.

F. Statistical Analysis

All results were presented as mean+standard deviation plotted using Origin 8. Student's t-test was applied to check the statistical significance ($*p<0.05$, $p<0.01$, $*p<0.001$).

Results

A. Current-Voltage Characteristics of Discharge

FIG. 2A shows the current-voltage characteristics of the discharge with air gap at distance of 2-10 mm. With gap increasing, the discharge current decreases while discharge voltage increases. Similar features of the discharge voltage increasing with air gap length are found in the case of electrolyte anode/cathode discharge. See, Bruggeman, P. et al. DC excited glow discharges in atmospheric pressure air in pin-to-water electrode systems. *Journal of Physics D: Applied Physics* 41, 215201 (2008). The self-organized pattern appears at the plasma-liquid interface and the discharge is stabilized when the air gap length is about 6 mm. At 2 mm gap, the discharge voltage is low while discharge current is high, and the discharge pattern represents a single filament. As the air gap length increases from 2 mm to 4 mm, the anode spot changes to a double ring-like structure. At an air gap length of 4 mm, the double ring structure is a solid inner circle surrounded by a continuous outer circle. At an air gap length of 6 mm, the double ring structure is a solid inner circle surrounded by a discontinuous continuous outer circle formed of a plurality of circular dots. At air gap length of 8 mm, various types of self-organized patterns are formed above the liquid media surface as shown in FIG. 2A. When the air gap is 2 to 8 mm, the plasma discharge is stable. When the air gap is 10 mm however, the plasma discharge becomes unstable. If the air gap is larger than 10 mm, the plasma discharge cannot be sustained.

B. Optical Spectrum of SOP Plasma

We have measured spectra of plasma from the plasma-liquid interface. Typical optical emission spectra are shown in FIG. 3. One can see that with air gap length increasing, the emission intensity decreases. The identification of the emission bands was performed according to the reference. See, Pearse, R. W. B. & Gaydon, A. G. *Identification of molecular spectra*. (Chapman and Hall, 1976). In the 250-300 nm wavelength range, weak emission bands (258, 267, and 284) were detected as NO lines. See, Walsh, J. L. & Kong, M. G. Contrasting characteristics of linear-field and cross-field atmospheric plasma jets. *Applied Physics Letters* 93, 111501 (2008).

Species at wavelengths of 337 and 358 nm were defined as $N_2$ $^3\Pi$ or NO $\beta$ $^2\Pi$ (denoted as $N_2$/NO), because both species have possible optical emission at these wavelengths. See, Pearse, R. W. B. & Gaydon, A. G. *Identification of molecular spectra*. (Chapman and Hall, 1976). The emission bands between 300 and 500 nm have still not been clearly identified in the literature. See, Chen, W. et al. Treatment of *Enterococcus faecalis* bacteria by a helium atmospheric cold plasma brush with oxygen addition. *Journal of Applied Physics* 112, 013304 (2012). However, we anticipated that OH was present at 309 nm, the wavelength of 375 nm could be indicative of $N_2^+/N_2$, and atomic oxygen (O) was denoted at the wavelength of 777 nm. Atomic oxygen (ground/excited states) is believed to have a significant effect on cells and therefore a broad biomedical application. See, Cheng, X. et al. The effect of tuning cold plasma composition on glioblastoma cell viability. *PloS one* 9, e98652 (2014). The dominant species of the spectra in these experiments are NO or N2 lines (258, 267, 337, and 357 nm), OH (309 nm), $N_2^+$ (391 nm), and O (777 nm).

C. $H_2O_2$ and $NO_2^-$ Concentration

Plasma species penetrate through the plasma-liquid interface and can produce chemically reactive species in the saline solution. Complex chemistry is associated with plasma produced species in liquid. See, Chen, Z., Cheng, X., Lin, L. & Keidar, M. Cold atmospheric plasma discharged in water and its potential use in cancer therapy. *Journal of Physics D: Applied Physics* 50, 015208 (2017). These reactions lead to the formation of short- and long-lived species. $H_2O_2$ and $NO_2^-$ are relatively long-lived species in the plasma-activated saline solution. The air gap length dependencies of the $H_2O_2$ and $NO_2^-$ concentrations in the plasma-activated saline solution with gap distance as a parameter are shown in FIG. 4. The concentration of $H_2O_2$ increased initially with air gap up to 4 mm then decreased except 10 mm as shown in FIG. 4a. The concentration of $NO_2^-$ increases with air gap from 2 mm to 8 mm, then decreases at 10 mm.

D. Cell Viability of H6c7 and BxPC-3

To investigate the potential of plasma-activated saline solution, we treated BxPC-3 human pancreas cancer cells and H6c7 human normal cells with them. RPMI, KSFM, and untreated saline solution were used as controls. FIG. 5 shows the cell viability of BxPC-3 human pancreas cancer cells and H6c7 human pancreas normal cells exposed to RPMI/KSFM, saline solution, and plasma-activated saline solutions for 24 h and 48 h. We can see that plasma-activated saline solutions have stronger effect on the cancer cells than that on the normal cells. For BxPC-3 cancer cells, when incubated for 24 h and 48 h, cell viability decreased firstly then increased with air gap length increasing. The minimum cell viability appears at 4 mm air gap. For H6c7 normal cells, when incubated for 24 h and 48 h, plasma with SOP at 6 mm air gap has the most significant effect of plasma-activated saline solutions.

In the past it was found that under some conditions cold atmospheric plasma can be directly applied to cancer cells without influencing the healthy tissues. Keidar, M. et al. Cold plasma selectivity and the possibility of a paradigm shift in cancer therapy. *British journal of cancer* 105, 1295-1301 (2011); Keidar, M. Plasma for cancer treatment. *Plasma Sources Science and Technology* 24, 033001 (2015); Yan, D., Sherman, J. H. & Keidar, M. Cold atmospheric plasma, a novel promising anti-cancer treatment modality. *Oncotarget* 8, 15977-15995 (2017); Karki, S. B., Thapa Gupta, T., Yildirim-Ayan, E., Eisenmann, K. M. & Ayan, H. Investigation of non-thermal plasma effects on lung cancer cells within 3D collagen matrices. *Journal of Physics D Applied Physics* 50 (2017); and Karki, S. B., Yildirim-Ayan, E., Eisenmann, K. M. & Ayan, H. Miniature Dielectric Barrier Discharge Nonthermal Plasma Induces Apoptosis in Lung Cancer Cells and Inhibits Cell Migration. *BioMed research international* 2017 (2017)

Figure 2B:
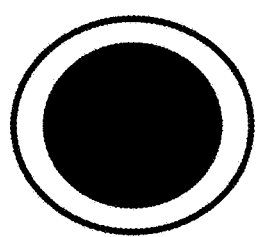
FIG. 2B is a diagram of a double ring self-organized pattern with a solid inner ring and a continuous outer ring in accordance with a preferred embodiment of the present invention.
Figure 2C:
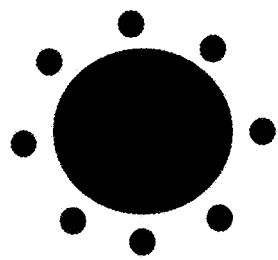
FIG. 2C is a diagram of a double ring self-organized pattern with a solid inner ring and a discontinuous outer ring in accordance with another preferred embodiment of the present invention.
Figure 3A:
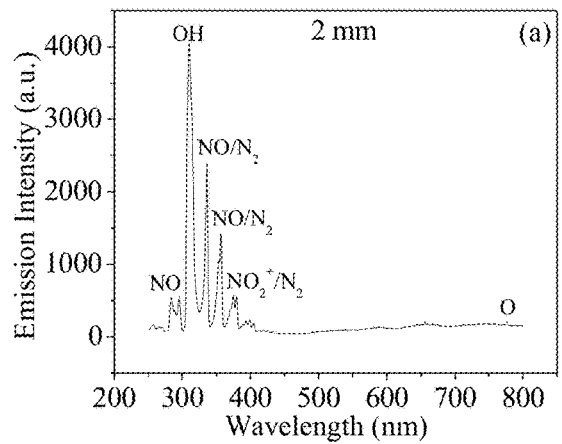
FIGS. 3A-3E show the Optical emission spectrum by the SOP plasma discharge above saline solution with different air gap length taken using UV-visible-NIR in the 200-850 nm wavelength range: (a) 2 mm, (b) 4 mm, (c) 6 mm, (d) 8 mm, and (e) 10 mm.
Figure 3B:
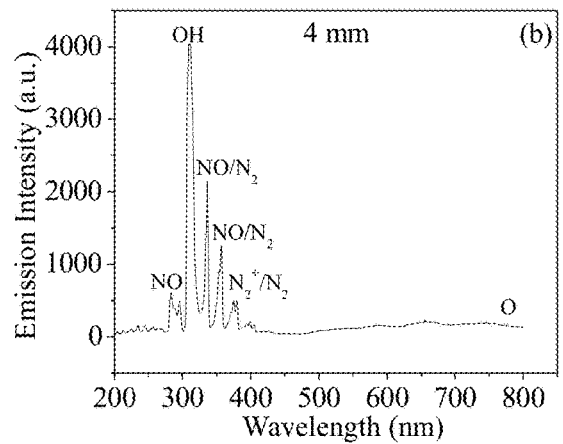
Figure 3C:
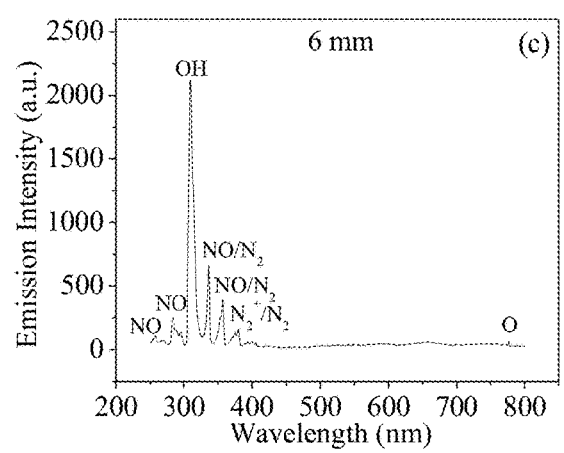
Figure 3D:
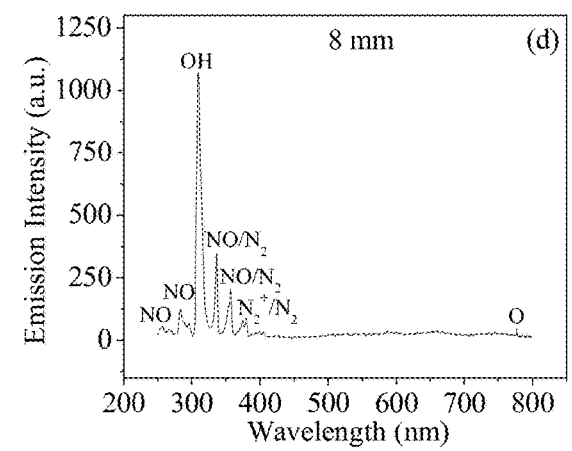
Figure 3E:
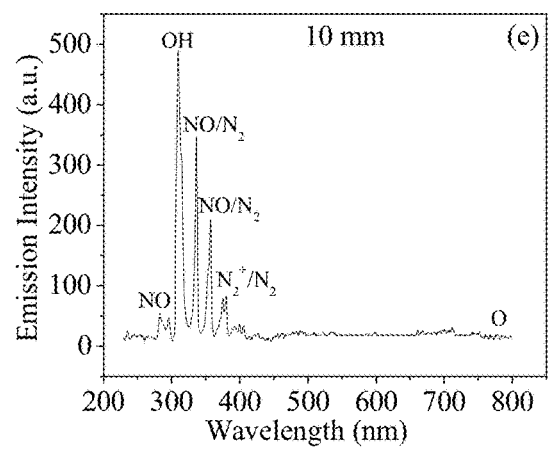

At the same time plasma-activated media have been explored and found to have a cytotoxic effect in oncology. In the above experiments, saline solutions were treated by plasma with various SOPs to be applied to human pancreatic cancer and normal cells. Discharge is formed between pin and liquid electrode and result in SOP formation dependent on discharge gap as shown in FIG. 2A. Transport of ROS/RNS across the plasma/liquid interface is affected by SOP. As such modification of saline solution by discharge is affected and controlled by SOP at the plasma-liquid interface. Typical optical emission spectra of such plasmas at different air gap were shown in FIG. 3 indicating that plasma at each air gap length contains ROS and RNS in the gas phase. ROS and RNS were also formed in plasma-activated saline solution. RNS are well known to induce cell death via DNA double-strand breaks and apoptosis, where ROS are capable of inducing the apoptosis and necrosis. See, Boehm, D., Heslin, C., Cullen, P. J. & Bourke, P. Cytotoxic and mutagenic potential of solutions exposed to cold atmospheric plasma. *Scientific reports* 6, 21464 (2016) and Kim, S. J. & Chung, T. Cold atmospheric plasma jet-generated RONS and their selective effects on normal and carcinoma cells. *Scientific reports* 6, 20332 (2016). Our results in FIG. 4 show that the $H_2O_2$ concentration is highest at 4 mm air gap distance while $NO_2^-$ concentration is highest at 8 mm air gap distance. Possible reactions illustrating the routes of $H_2O_2$ and $NO_2^-$ formation in liquid and plasma have been reported in our previous articles[32,40,41]. See, Chen, Z., Cheng, X., Lin, L. & Keidar, M. Cold atmospheric plasma discharged in water and its potential use in cancer therapy. *Journal of Physics D: Applied Physics* 50, 015208 (2017); Chen, Z., Lin, L., Cheng, X., Gjika, E. & Keidar, M. Treatment of gastric cancer cells with nonthermal atmospheric plasma generated in water. *Biointerphases* 11, 031010 (2016); and Chen, Z., Lin, L., Cheng, X., Gjika, E. & Keidar, M. Effects of cold atmospheric plasma generated in deionized water in cell cancer therapy. *Plasma Processes and Polymers* 13, 1151-1156 (2016). From FIG. 2 Awe can see that plasma average discharge power is growing with increasing air gap, which results in the temperature of plasma-activated saline solutions going up (except 10 mm). Since $H_2O_2$ is thermodynamically unstable, its rate of decomposition increases with rising temperature. See, Goss, D. J. & Petrucci, R. H. *General Chemistry Principles & Modern Applications, Petrucci, Harwood, Herring, Madura: Study Guide*. (Pearson/Prentice Hall, 2007). It should be pointed out that the plasma discharge becomes unstable at the air gap length of about 10 mm. The discharge must be re-ignited. As such, the discharge instability at 10 mm gap might lead to a low concentration of nitrite. FIG. 5 shows that plasma-activated saline solution affects cancer and normal pancreatic cells in a selective manner. Plasma with SOP activating saline solutions have more effect on cancer cells. The trend of pancreatic normal and cancer cells can be attributed to the trend of ROS and RNS concentration with different air gap distances. On the other hand, $H_2O_2$ reacts with $NO_2^-$ to form peroxynitrite $OONO^-$ and $H_2O$. See, Tian, W. & Kushner, M. J. Atmospheric pressure dielectric barrier discharges interacting with liquid covered tissue. *Journal of Physics D: Applied Physics* 47, 165201 (2014). $ONOO^-$ is a powerful oxidant and nitrating agent that is known to be a much more damaging to cancer cells[44]. See, Beckman, J. S. & Koppenol, W. H. Nitric oxide, superoxide, and peroxynitrite: the good, the bad, and ugly. *American Journal of Physiology-Cell Physiology* 271, C1424-C1437 (1996). Therefore, a synergistic effect of ROS and RNS is suspected to play a key role in the apoptosis of the plasma solutions. For BxPC-3 cancer cells, intracellular ROS-mediated up-regulation of DR5 can leads to apoptosis (procaspase-8 is a direct downstream target of DR5). See, Kong, R. et al. Dihydroartemisinin enhances Apo2L/TRAIL-mediated apoptosis in pancreatic cancer cells via ROS-mediated up-regulation of death receptor 5. *PLoS One* 7, e37222 (2012). On the other hand, intracellular generation of ROS induces increasing protein expression of Bax, disruption of the mitochondrial membrane potential and release of cytochrome c and AIF into the cytosol resulting in to the activation of caspase9/3 cascade. See, Zhang, R., Humphreys, I., Sahu, R. P., Shi, Y. & Srivastava, S. K., "In vitro and in vivo induction of apoptosis by capsaicin in pancreatic cancer cells is mediated through ROS generation and mitochondrial death pathway," *Apoptosis* 13, 1465-1478 (2008). Therefore, plasma with SOP-induced intracellular generation of ROS induced apoptosis in BcPC-3 cancer cells might be orchestrated by the synergistic effects of both extrinsic and intrinsic pathways. The results indicate the cytotoxicity of plasma-activated saline solution is specific to pancreatic adenocarcinoma cancer cells. The plasma-activated saline solution at 4 mm air gap distance had the most significant affect in inducing cell death in pancreatic cancer cells. This is related to certain amounts of ROS and RNS generated by double ring-like structure plasma with SOPs The above experiments demonstrate that self-organized pattern plasma-activated saline solutions applied to both BxPC-3 human pancreatic cancer and H6c7 human pancreatic normal cells exhibit selective manners. The air gap at a distance between 2 and 10 mm results into various shapes of self-organized patterns (SOPs) on saline solution anode. A synergistic effect of RNS and ROS present in the plasma solution is suspected to play a key role in the cell death. The SOP plasma-activated saline solution at 4 mm air gap distance had the most significant affect in inducing cell death in both pancreatic normal and cancer cells. The SOP plasma-activated saline solutions have more serious effect on BxPC-3 human pancreatic adenocarcinoma cancer cells than H6c7 human pancreatic epithelial normal cells. These results suggest that SOP plasma-activated saline solutions can be used with anti-tumor effect for clinical applications.

Breast Cancer Experiments

Figure 6A:
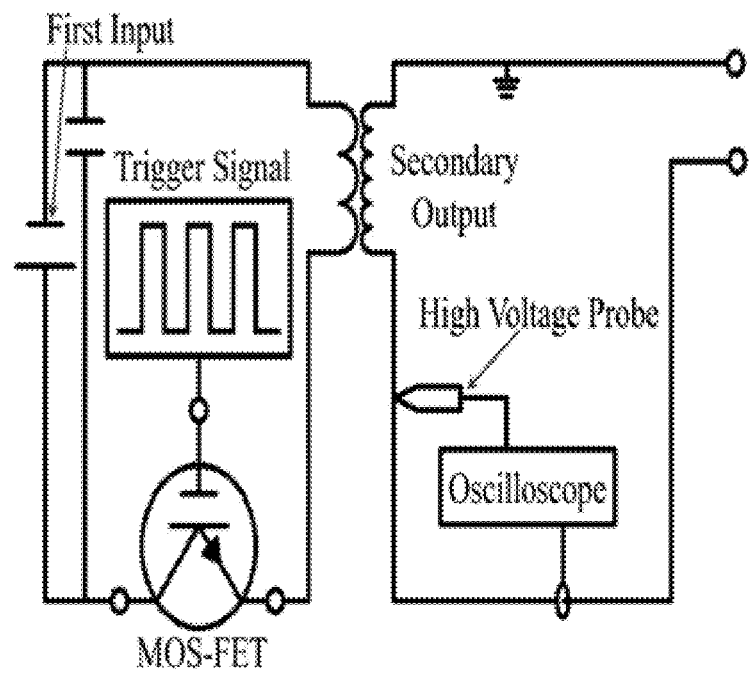
FIG. 6A is a schematic representation of AC power used in the experiments showing the effect on breast cancer cells.
Figure 6B:
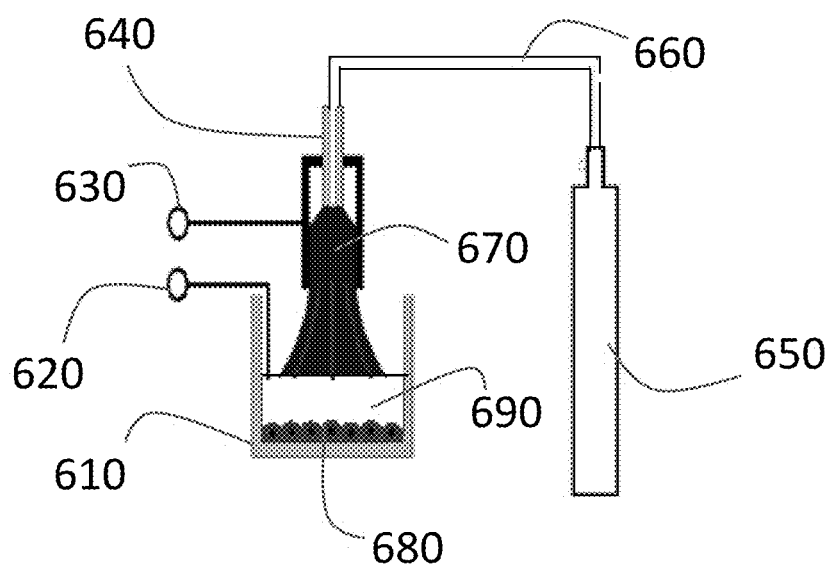
FIG. 6B is a schematic representation of the He SOP plasma discharge setup used in the experiments. Around 10 mm gap between the electrode and surface of liquid accommodated plasma.

FIG. 6A shows a schematic representation of the AC power and FIG. 6B shows the self-organized pattern ("SOP") plasma discharge setup. The discharge modes and self-organized patterns were organized as follows. The system has a gas source 650 (e.g., helium) with tubing 660 for conveying the gas to a delivery means 640, which may be a tube, handpiece, nozzle or other delivery means. A lower electrode 620 was connected with cultured media (1 mL media containing cancer cells). The upper electrode 630 (inner diameter Ø=4 mm) was then installed above the upper surface of the media 690. An AC power supply unit (FIG. 6A) was fabricated at The George Washington University. As shown in FIG. 6A, the electrode 620 was connected to ground. A voltage was applied between the two electrodes 620, 630, and the gap between electrode 630 and the surface of the liquid media 690 becomes filled with plasma 670. A gas flow rate at 1.0 L/min as basic platforms for the bio-oriented studies. SOP plasma discharge setup is capable of producing well-defined self-organized patterns between electrode 630 and the surface of the liquid media 690 facing the plasma. Cultured media containing cells 680 were treated by SOP plasma with 90 seconds' duration at input voltage 6V, 8V, 10V, and 12V.

While the above-described system for generating cold plasma was used in the experiments, other types of cold plasma systems such as those described in U.S. Pat. Nos. 10,213,614 9,999,462 or International Application Publication WO 2018/191265 may be used to generate cold plasma. The aforementioned patents and application are hereby incorporated by reference in their entirety.

UV-visible-NIR, a range of wavelength 200-850 nm, was investigated on plasma to detect various RNS and ROS (nitrogen [$N_2$], nitric oxide [—NO], nitrogen cation [$N^{+2}$], atomic oxygen [O], and hydroxyl radical [—OH]). The spectrometer and the detection probe were purchased from Stellar Net Inc. In order to measure the radius of the He SOP plasma-activated saline solution and DI water, the optical probe was placed at a distance of 2 cm in front of plasma. Integration time of the collecting data was set to 100 ms.

The human breast cancer cell lines: MDA-MB-231 and MCF-7 were provided by Dr. Zhang's lab at the George Washington University. Cells were cultured in Dulbecco's Modified Eagle Medium (DMEM, Life Technologies) supplemented with 10% (v/v) fetal bovine serum (Atlantic Biologicals) and 1% (v/v) penicillin and streptomycin (Life Technologies). Cultures were maintained at 37° C. in a humidified incubator containing 5% (v/v) $CO_2$.

A fluorometric hydrogen peroxide assay Kit (Sigma-Aldrich, St. Louis, Mo., USA) was used for measuring the amount of $H_2O_2$, according to the manufacturer's protocol. Briefly, 50 µL of standard curve, control, and experimental samples were added to 96-well flat-bottom black plates, and then 50 µL of Master Mix was added to each of well. The plates were incubated for 20 min at room temperature protected from light and fluorescence was measured by a Synergy H1 Hybrid Multi-Mode Microplate Reader at Ex/Em: 540/590 nm.

RNS level were determined by using the Griess Reagent System (Promega Corporation) according to the instructions provided by the manufacturer. Briefly, we added 50 µl of standard curves samples, controls, and experimental samples to the 96-well flat-bottom plates. Then dispense 50 µl of the Sulfanilamide Solution to all samples and incubate 5-10 minutes at room temperature. Finally, dispense 50 μl of the NED solution to all wells and incubate at room temperature 5-10 minutes. The absorbance was measured at 540 nm by Synergy H1 Hybrid Multi-Mode Microplate Reader.

XTT sodium salt ((2,3-bis(2-methoxy-4-nitro-5-sulfophenyl)-5-[(phenylamino)carbonyl]-inner salt-2H-tetrazolium, monosodium salt)) solution, purchased from Cayman chemical, was prepared by dissolving XTT power in DMEM. XTT sodium salt solution (1000 μper well, 500 μM) in a 12-well flat-bottom plate by SOP plasma with input 6 V, 8 V, 10 V, and 12 V for 90 seconds. As a control, untreated XTT sodium salt solution in triplicate were transferred to a 12-well flat-bottom plate. The color change of XTT solution indicates the presence of superoxide ($O_2^-$). Color change of XTT solution was measured by Hach DR 6000 uv vis spectrophotometer at 470 nm.

The MDA-MB-231 and MCF-7 cancer cells were plated in 12-well flat-bottom microplates at a density of $1 \times 10^5$ cells per well in 1000 μL of complete culture medium. Cells were incubated for 24 hours to ensure proper cell adherence and stability. On day 2, SOP plasma treated each wells for 90 seconds at input voltage 6, 8, 10, and 12 V. Cells were further incubated at 37° C. for 24 and 48 hours. The cell viability of the breast and pancreas adenocarcinoma cancer cells was measured for each incubation time point with an MTT assay. 1000 μL of MTT solution (3-(4, 5-dimethylthiazol-2-yl)-2,5-diphenyltetrazolium bromide) (Sigma-Aldrich) was added to each well followed by 3-hour incubation. The MTT solution was discarded and 1000 μL per well of MTT solvent (0.4% (v/v) HCl in anhydrous isopropanol) was added to the wells. The absorbance of the purple solution was recorded at 570 nm with the Synergy H1 Hybrid Multi-Mode Microplate Reader.

Cells were seeded in 12-well plates at a density of $1 \times 10^5$ cells/well. Cells were incubated for 24 hours to ensure proper cell adherence and stability. After SOP plasma treatment with different input voltage, both breast cancer cells were collected and stained with fluorescein isothiocyanate (FITC)-conjugated Annexin V and 7-Aminoactinomycin D (7-AAD) obtained from BD Biosciences (San Jose, Calif.). Flow cytometry was performed using FACS Calibur (BD Bioscience, San Jose, Calif.); results were analyzed using FlowJo software (Ashland, Oreg.).

After treatment with SOP plasma, both breast cancer cells were cultured for the indicated time, washed first with PBS and then with PBS containing 0.05% TritonX-100 for 30 seconds before fixation with 4% paraformaldehyde for 10 min at room temperature. Cells were then washed and incubated for 10 min in blocking buffer (PBS containing 3% BSA and 0.02% Tween-20) and subsequently incubated for 1-2 hour with a primary antibody at room temperature. Cells were washed three times with PBS-T (PBS containing 0.02% Tween-20) and then incubated with a secondary antibody (rabbit Alexa Fluor-594 and mouse Alexa Fluor-488 were from Life Technology) for 1 hr. After washing with PBS-T, cells were mounted with Fluoromount G (Southern-Biotech) containing DAPI. Slides were imaged using microscope.

MDA-MB-231 and MCF-7 cancer cells were treated with different input voltage of cold plasma for 90 seconds. Cells were trypsinized and subjected to a neutral comet assay using the Trevigen Comet assay kit following the manufacturer's protocol. Cells were imaged using the Zeiss fluorescent microscope. Comet tails were measured using the CometScore software and quantified. At least a total of fifty cells were measured per treatment.

Cells were washed using 1×PBS and lysed on ice using RIPA buffer containing 1× protease inhibitors (Roche) and 1× PhosphoStop (Roche). 10-20 μg of protein was separated on a 4-15% SDS-PAGE gradient gel (Biorad). The separated proteins were transferred onto a PVDF (Biorad) membrane. The membrane was blocked in blocking buffer [100 mM Tris-HCl pH 7.4, 0.1% Tween20, 150 mM NaCl and 5% (w/v) nonfat milk] for 1 h and incubated with primary antibodies in blocking buffer at 1:1000 dilution, The membrane was developed with ECL chemiluminescence (Amersham Pharmacia) after incubation with appropriate secondary antibody diluted to 1:5000 in the blocking buffer. Band intensity was normalized with GAPDH as a loading control.

Figure 7:
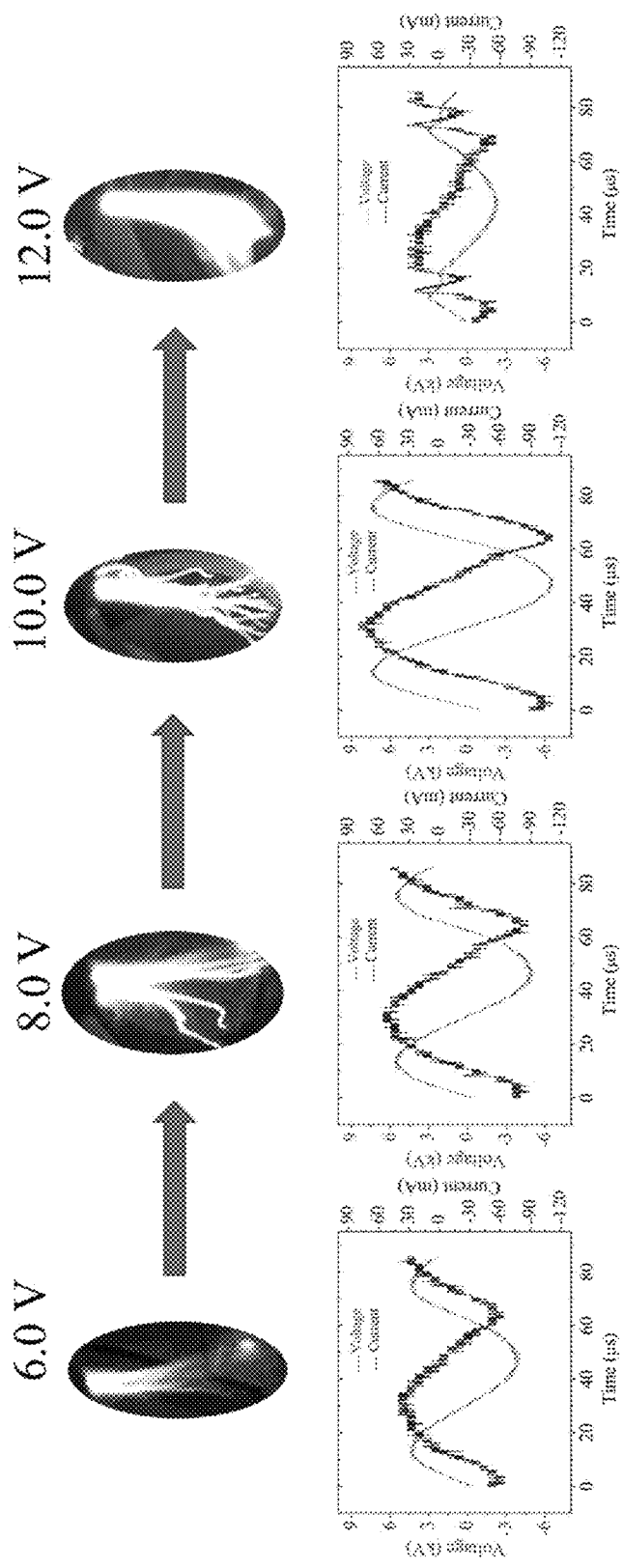
FIG. 7 is a series of optical photographs and graphs of discharge votage of SOP plasma activated saline solutions at flow rate of 1.0 L/min with different input voltages: 6 V, 8 V, 10 V, and 12 V.
Figure 8A:
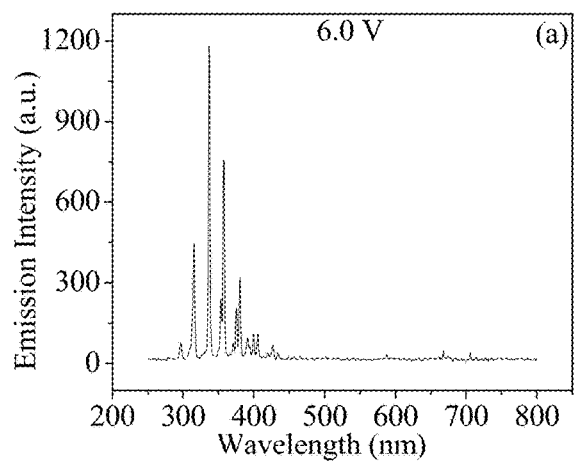
FIGS. 8A-8D show optical emission spectra of He SOP plasma activated saline solutions at flow rate of 0.6 L/min with different input voltages: (3A) 6 V, (3B) 8 V, (3C) 10 V, and (3D) 12 V.
Figure 8B:
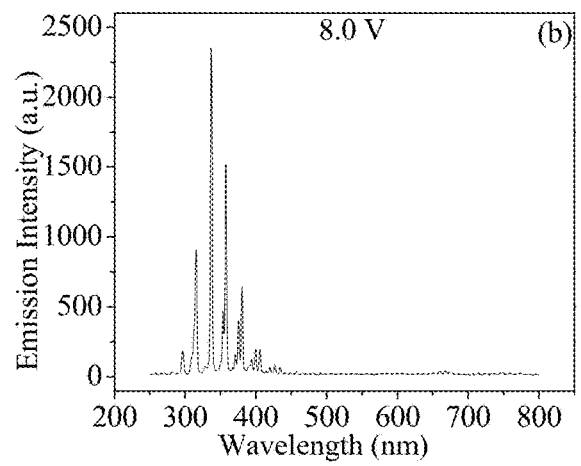
Figure 8C:
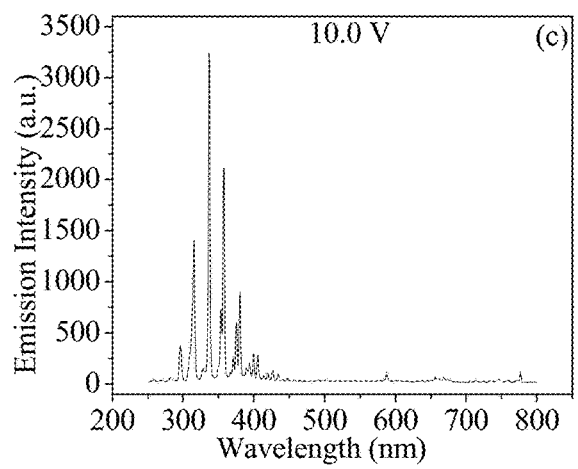
Figure 8D:
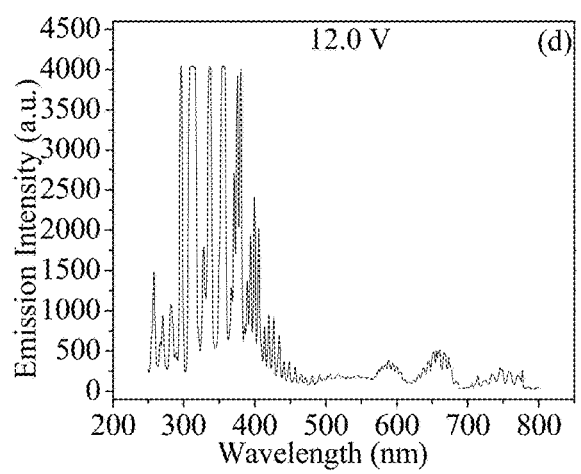

FIG. 7 shows optical photographs and discharge voltage of SOP plasma activated saline solutions at a flow rate of 1.0 L/min with input voltage of 6V, 8V, 10V, and 12V. The input voltage characteristics of SOP plasma activated culture medium (DMEM) can be divided into three stages. At stage I (6V input voltage), the discharge voltage is relatively low, and the discharge modes represent glow discharge. As the discharge voltage and current increase to a certain degree (8V and 10 V input voltage), the discharge modes change from glow discharge (Stage I) to spark discharge (Stage II). Complex discharge modes consisting of multi-filaments and confocal lines of different density are produced. The discharge stabilizes at the multi-filament mode. Then, the discharge enters an arc discharge mode (Stage III, 12 V input voltage), resulting in drastically enhanced heat radiation. The discharge flips from the multi-lament and heat radiation-supported stage where the thermionic emission is enough to maintain the discharge current.

We have measured spectra of plasma from the plasma-DMEM interface. Typical optical emission spectra are shown in FIGS. 8A-8D. The emission intensity increases with increasing input voltage, and the intensity at 12V input voltage is over a range of UV-visible-NIR. The identification of the emission bands was performed according to Pearse et al. In the 250-300 nm wavelength range, relative weak emission bands (258, 267, and 297) were detected as NO lines. Species at wavelengths of 337 and 357 nm were defined as $N_2$ $C_3\Pi u$ or NO $\beta^3\Pi g$ (denoted as $N_2$/NO), because both species have possible optical emission at these wavelengths. The emission bands between 300 and 500 nm have still not been clearly identified in the literature. However, we anticipated that OH was present at 309 nm, the wavelength of 391 nm could be indicative of $N_2+/N_2$, and atomic oxygen (O) was denoted at the wavelength of 777 nm. The features were assigned as helium (He) lines between 550-750 nm. The dominant species of the spectra in He SOP activated saline solution were NO or $N_2$ lines (258, 267, 297, 337, 357, and 381 nm), OH (309 nm), $N_2^+$ (391 nm), and O (777 nm).

Figure 9A:
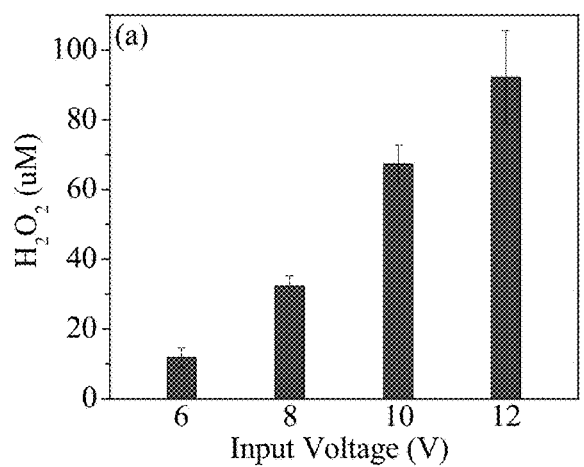
FIGS. 9A-9C show 4 ROS and RNS concentration of media treated by SOP plasma with input 6V, 8V, 10V, and 12V for 90 seconds. (4A) $H_2O_2$ concentration, (4B) $NO_2^-$ concentration, and (4C) Relative intensity of superoxide.
Figure 9B:
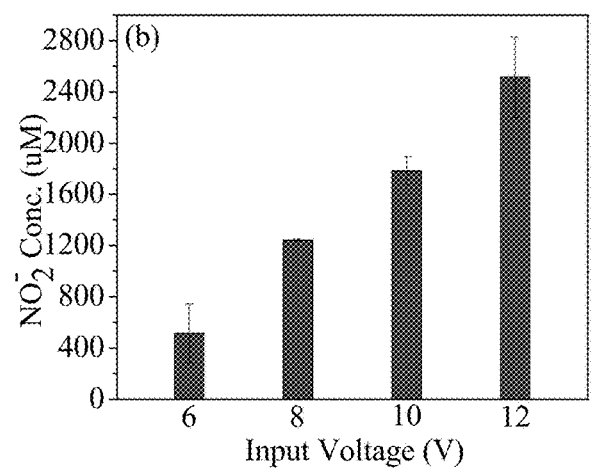
Figure 9C:
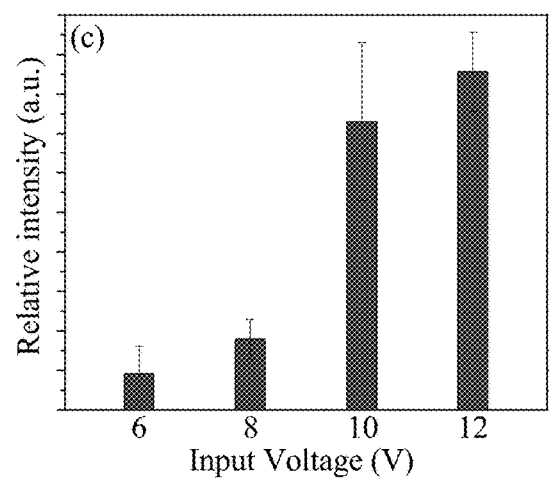

Plasma treatment of DI water and DMEM were performed to induce changes in the concentration of ROS and RNS as a function of the treatment time. Indeed, as shown in FIG. 9A, $NO_2^-$ concentration in DMEM increase with the input voltage. The $NO_2^-$ mainly originates as NO ($N_2$+ e→2N+e, N+$O_2$→NO+O, 4NO+$O_2$+2$H_2O$→4$NO_2^-$+4$H^+$), while most of NO is formed in the gas phase during the afterglow a few milliseconds after the discharge pulse. In FIG. 9B, ROS concentration dependence on input voltage in SOP plasma treated DMEM is illustrated. $H_2O_2$ generation might be attributed to the high electron density and energy of the plasma (He→$He^+$+e, $He^+$+$H_2O$→$H_2O^+$+He, $H_2O^+$+ $H_2O$→$H_3O^+$+.OH; He+e→$He^*$+e, $He^*$+$H_2O$→He+.OH+ H.; $H_2O$+e→$H_2O^*$+e, $H_2O^*$→.OH+H.; .OH+.OH→$H_2O_2$). The $H_2O_2$ concentration increases with the input voltage in DMEM. XTT solution was used to determine the relative concentration of superoxide ($O_2^-$). The tetrazolium dye XTT was reduced their soluble formazans by superoxide radicals produced by the oxidation of xanthine by xanthine oxidase under standard conditions. FIG. 9C shows the relative superoxide concentration of DMEM treated by SOP plasma for 6V, 8V, 10V, and 12V for 90 seconds. Relative intensity increases with input voltage, which means relative concentration of superoxide increasing with treatment.

Figure 10A:
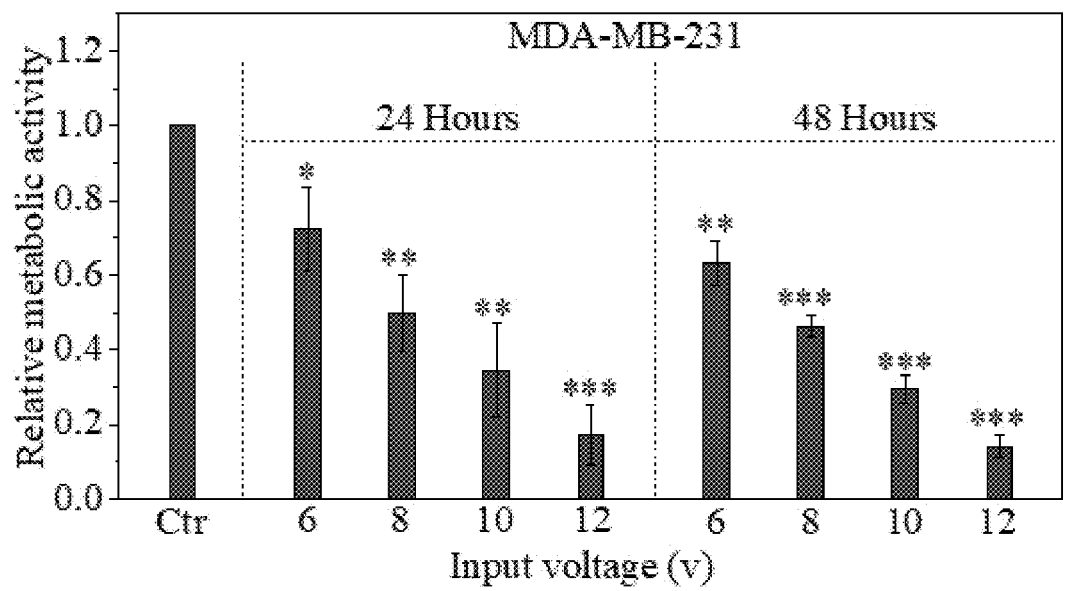
FIGS. 10A-10B show cell viability of MDA-MB-231 and MCF-7 treated by SOP plasma with input 6, 8, 10, and 12 V. 24 and 48 hours' cell viability of MDA-MB-231 breast cancer cells (a), and 24 and 48 hours' cell viability of MCF-7 cancer cells (b). The ratios of surviving cells for each cell line were calculated relative to controls (without treatment). Student t-test was performed, and the statistical significance compared to cells present in control is indicated as *$p<0.05$, $p<0.01$, *$p<0.001$. (n=3).
Figure 10B:
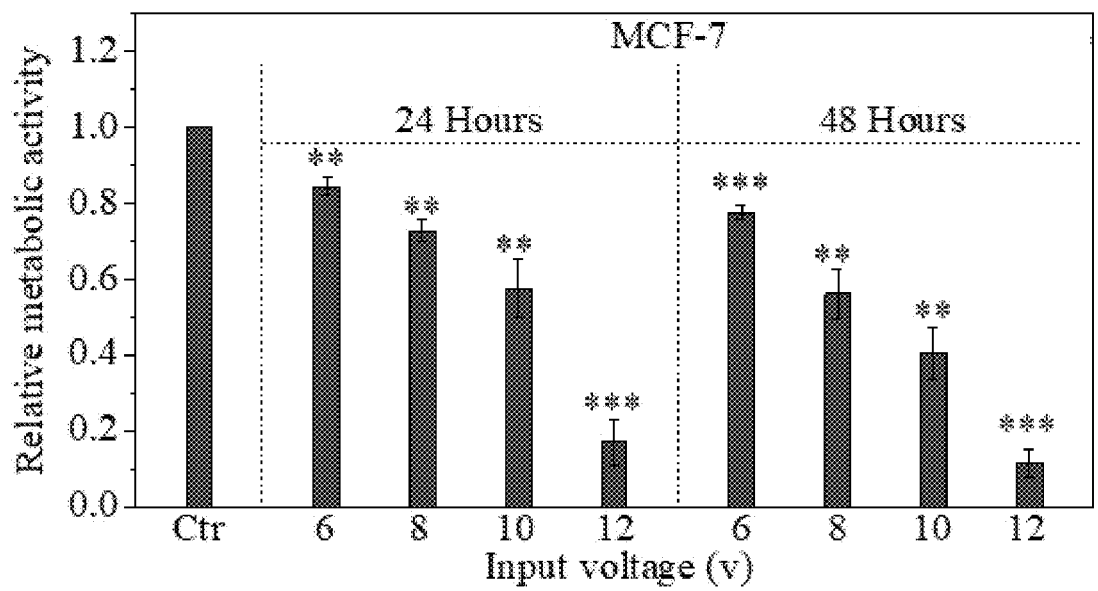

FIGS. 10A-10B show the cell viability of the breast cancer cells MDA-MB-231 and MCF-7 after 24 and 48 hours' incubation with SOP plasma with input 6, 8, 10, and 12V. For MDA-MB-231 cancer cells (FIG. 10A), the cell viability decreased with input voltage increasing, especially dropping significantly at input voltage 12V. As seen in the figure, the 48 hour cell viability was lower than 24 hour at each input voltage. The similar effect on MCF-7 cancer cells was also observed (FIG. 10B). Comparing both breast cancer cells, SOP plasma had much stronger effect on MDA-MB-231 than MCF-7.

To investigate the types of cell death induced by SOP plasma, SOP plasma treated or untreated MDA-MB-231 and MCF-7 cancer cells were stained with Annexin V/7-AAD and analyzed by flow cytometry. Four-quadrant analysis of the flow-cytometry result characterizes the cells. Cells are 7-AAD-negative and Annexin V-positive classified as early apoptotic cells. Late apoptotic cells are positive for both 7-AAD and Annexin V. Cells undergoing necrotic death are usually 7-AAD-positive and Annexin V-negative. Percentages of stained cells in the treatment groups demonstrated a clear pro-apoptotic effect. Comparing both breast cancer cells, MCF-7 appeared to display a higher percentage of necrotic effect than MDA-MB-231 in cell distributions. These results showed that SOP plasma efficiently induced apoptotic pathway and necrosis in MDA-MB-231 and MCF-7.

Figure 12A:
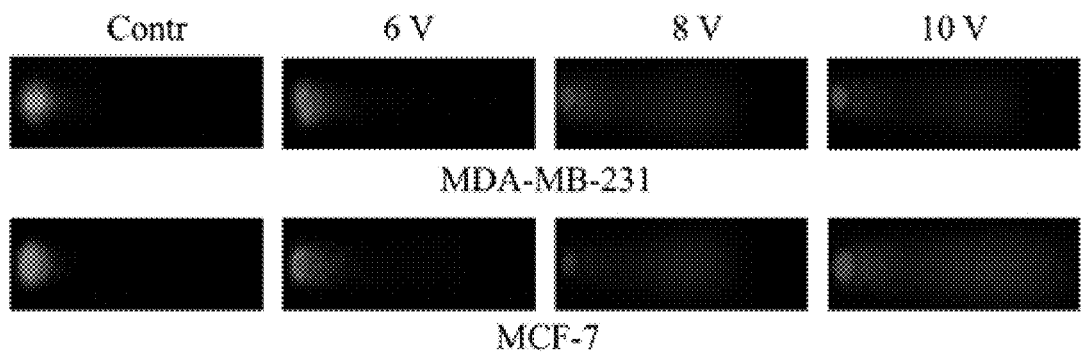
FIGS. 12A-12C show SOP plasma treatment induces high levels DNA damage in both breast cancer cells MDA-MB-231 and MCF-7.
Figure 12B:
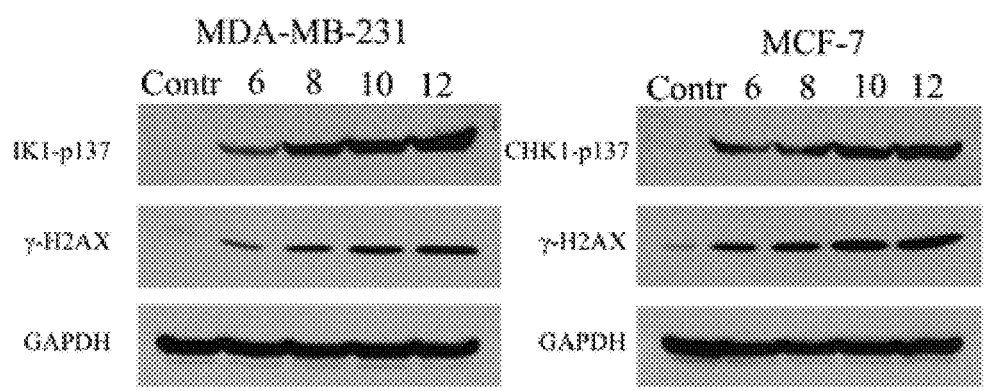
Figure 12C:
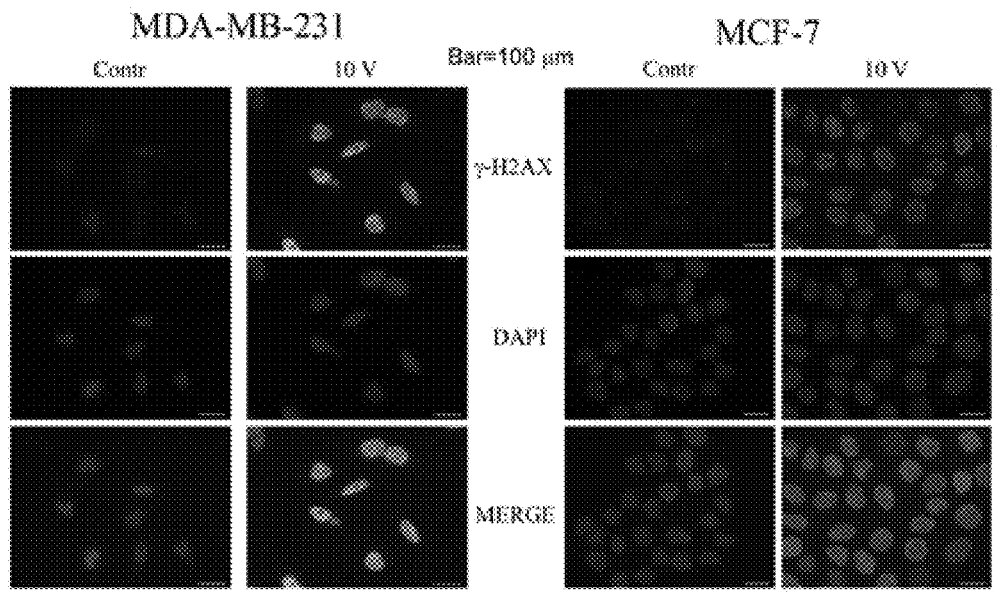

FIG. 12A shows that neutral comet assay performed on the cancer cells MDA-MB-231 and MCF-7 treated with input voltage of 6V, 8V, 10V, and 12V for 90 seconds show significant difference in comet tails compared to control cells. The results indicate that DNA damage of both breast cancer cells treated by SOP plasma increased with input voltage from 6V to 12V. Western blot shows that after treatment with input voltage of 6V, 8V, 10V, and 12V for 90 seconds, cells show increased in the DNA damage marker γ-H2AX and cell cycle checkpoint CHK1-p137 (FIG. 7B). FIGS. 12B and 12C show immunofluorescence staining in MDA-MB-231 and MCF-7 cells treated with 10V for 90 s. The graph shows both cancer cell lines display a higher γ-H2AX foci in treated cells compared to control.

Figure 11:
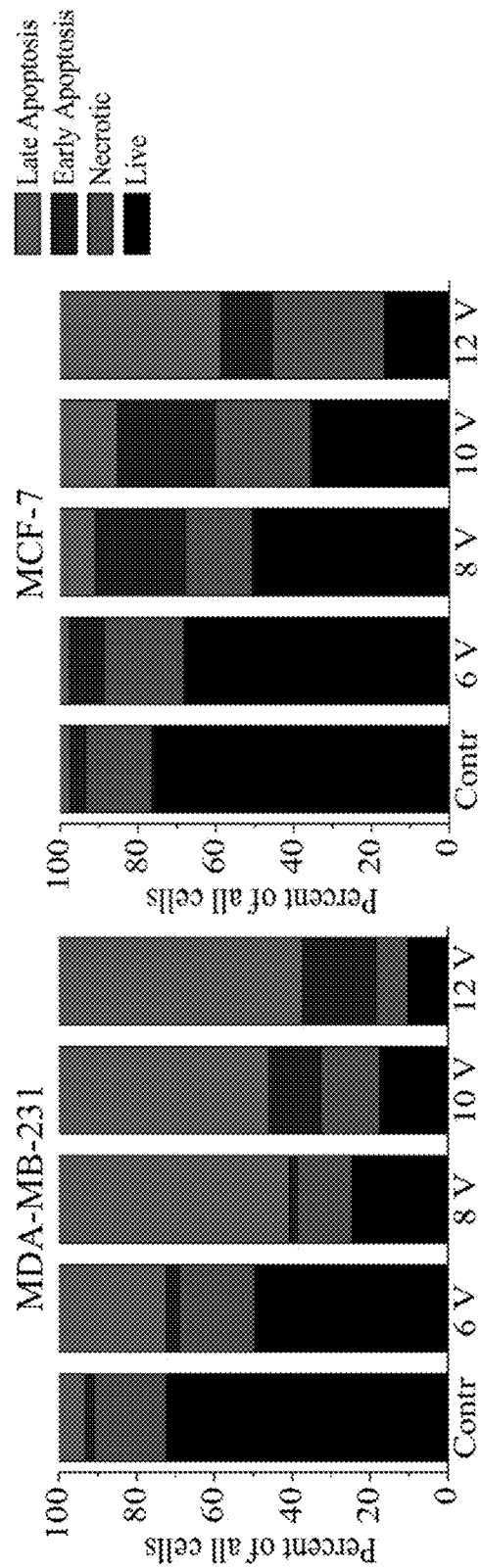
FIG. 11 shows cell staining with Annexin V and 7-AAD for detection of apoptosis of MDA-MB-231 and MCF-7. Numbers of viable cells are significantly decreased in cells treated by SOP plasma for 24 hours' durations of time.

SOP plasma contains the free radicals, reactive species, ultraviolet (UV) radiation, and the transient electric fields inherent with plasma delivery. It can be argued that UV photons are not the major SOP plasma species inducing production of RONS in solutions in our experimental setup (FIGS. 6A-6B), due to its wavelength of 200-280 nm. Radicals and electrons generated during SOP plasma formation can be both short-lived and long-lived. Short-lived radicals or species includes superoxide ($O_2^-$), nitric oxide (NO), atomic oxygen (O), ozone ($O_3$), hydroxyl radical (OH), singlet delta oxygen (SOD, $O_2(^1\Delta g)$), etc. Short-lived radicals or species react to form long-lived species including hydrogen peroxide ($H_2O_2$) and nitrite ($NO_2^-$). $H_2O_2$ and $NO_2^-$ concentration and relative $O_2^-$ concentration of SOP plasma-activated DMEM were shown in FIGS. 9A-9C. The current data employing the MTT assay showed that RONS generated by SOP plasma displayed a significant effect against two breast cancer cell lines MDA-MB-231 and MCF-7 (FIGS. 10A-10B). SOP plasma significantly inhibits cell proliferation via reduction of viability and induction of apoptosis (FIGS. 10A-10B and FIG. 11). Previous studies have shown that plasma induces RONS generation in cancer cells. SOP plasma generated species in DMEM containing .OH, NO, $O_2^-$, O, $O_2(^1\Delta g)$, $H_2O_2$ and $NO_2^-$ are prominent components of antitumor plasma action (FIG. 3 and FIG. 4). .OH derived amino acid peroxides can contribute to cell injury because .OH itself and protein (amino acid) peroxides are able to react with DNA, thereby inducing various forms of damage. Atomic oxygen (O) measured by OES (including the ground state and all the excited states) is believed to have a significant effect on cells (FIGS. 8A-8D). Superoxide ($O_2^-$) generated by plasma (related concentration measured by XXT) can activate mitochondrial-mediated apoptosis by changing the mitochondrial membrane potential and simultaneously up-regulating pro-apoptotic genes and down-regulating anti-apoptotic genes for activation of caspases resulting in cell death. Moreover, nitrite (NO) and superoxide ($O_2^-$) can easily form ONOO$^-$ once they collide. ONOO$^-$ is a powerful oxidant and nitrating agent, which is known to be highly damaging to tumor cells. However, there might be additional antitumor pathways related to $H_2O_2$ and $NO_2^-$. For example, $H_2O_2$ and $NO_2^-$ are believed to generate peroxynitrite ($H_2O_2+2NO_2^- \rightarrow 2HONOO^-$) and is known to be toxic to cells. When SOP plasma activates DMEM, the concentration of both $H_2O_2$ and $NO_2^-$ rises with input voltage (FIGS. 9A-9C), and synergism of $H_2O_2$ and $NO_2^-$ mentioned above might be an important factor. SOP plasma also produces significant amount of ozone ($O_3$), which is known to decrease cell viability. Ozone has a role in the formation of biologically active RONS in aqueous media, which may be responsible for cell death.

Figure 13:
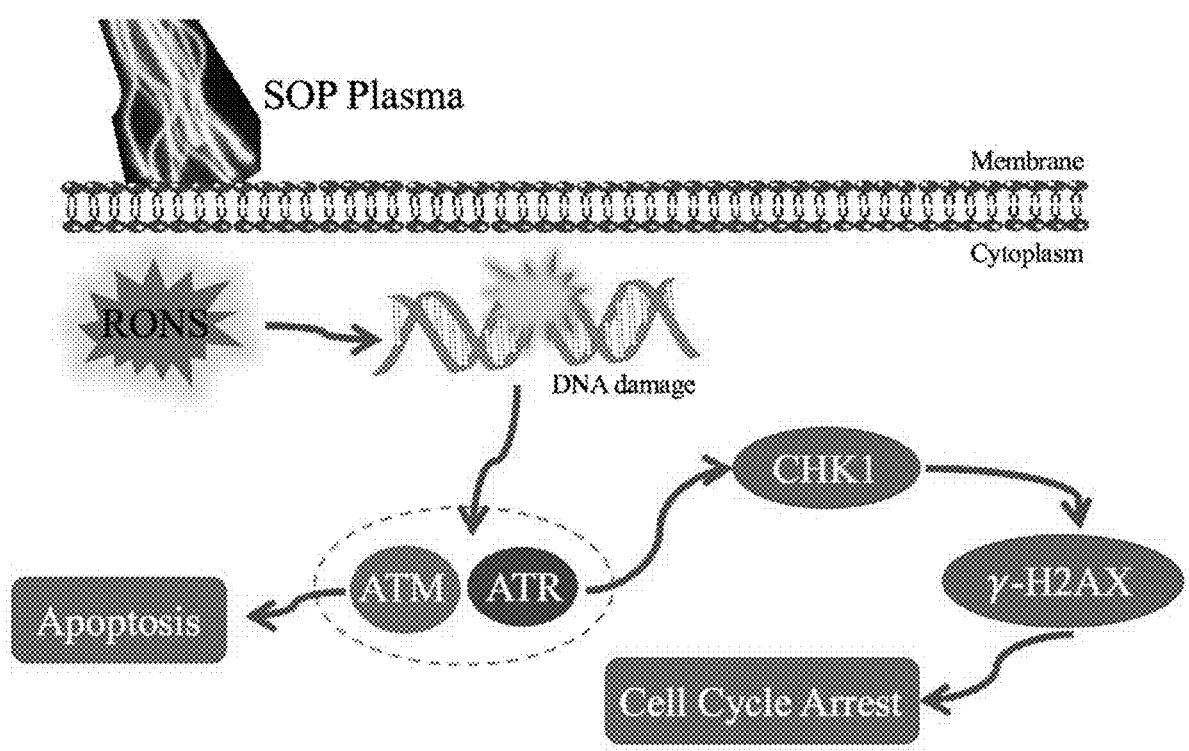
FIG. 13 illustrates the molecular mechanism of soft-jet plasma induced breast cancer cells' apoptosis.

Generation of RONS is either mitochondrial or enzyme dependent and affects several vital cellular functions, including differentiation and intracellular signaling. Oxidative stress is an important contributor to diseases, through its effect on DNA. Oxidative stress arises not only from increased levels of reactive oxygen species, but also from significant increase in concentrations of reactive nitrogen species, such as nitric oxide (NO) and peroxynitrite (ONOO$^-$). Experimental evidences reveal that plasma can cause cell damage and death through RONS signaling. SOP plasma inactivates a number of enzymes that are involved in cellular energy pathways, as well as DNA replication and repair. Cells respond to DNA damage either by halting cell cycle progression or by undergoing apoptosis, which might be coordinated primarily by the kinase signaling cascade and the checkpoint pathways. Western blotting analysis revealed that SOP plasma caused a dose-dependent increase in the expression levels of CHK1-p53 and γ-H2AX (FIG. 12B). CHK1 is a chromatin-associated protein that is phosphorylated by ATR and is the primary effector of intra-S. SOP plasma induced an apparent ROS-mediated DNA damage response, as evidenced by γ-H2AX staining. Furthermore, the key checkpoint kinases were involved in the DNA damage response (FIGS. 12A-12C). In addition, we ruled out the possibility that the DNA damage response was associated with DNA fragmentation during apoptosis but did not prevent phosphorylation of γ-H2AX. SOP plasma induced apoptosis, implying that the DNA-damaging effects of a single kinase inhibitor could be complemented by that of other kinase inhibitors. Taken together, our data showed that RONS generated by SOP plasma has a function in both DNA damage leading to apoptosis. Exposure of both breast cancer cell lines to SOP plasma in RONS-mediated DNA damage, activating the ATM/ATR kinase signaling cascades. ATR phosphorylates the checkpoint effector kinase Chk-1 activating γ-H2AX resulting in cell cycle arrest and induction of apoptosis. A schematic representation of SOP plasma induced apoptosis and cell cycle arrest is displayed in FIG. 13.

In summary, this treatment modality is capable of efficiently inhibiting the growth and proliferation of two breast cancer cell lines MDA-MB-231 and MCF-7. Our data demonstrated that SOP plasma induced ROS generation, which in turn resulted in DNA damage, activating the ATM/ATR kinase signaling cascades. ATR phosphorylates the checkpoint effector kinase Chk-1 activating γ-H2AX resulting in cell cycle arrest and ATM induce apoptosis of both cancer cell lines. These results provide new insight into the pro-apoptotic mechanism for SOP plasma.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for treatment of cancer cells comprising:
   positioning an electrode at a distance of less than 10 mm from a surface of a media in a container;
   flowing an inert gas from a source of inert gas past said electrode and onto said surface of said media in said container;
   applying electrical energy to said electrode with an electrosurgical generator while said inert gas is flowing past said electrode for a fixed period of time to generate a plasma self-organized pattern at a surface of said media to induce reactive oxygen and nitrogen species generation in said media; and
   exposing human cancer cells to said plasma activated media to cause DNA damage in said human cancer cells.

2. The method for treatment of cancer cells according to claim 1 wherein said step of treating human cancer cells with said plasma activated media comprises injecting said plasma activated media into an area of a human body containing said human cancer cells.

3. The method for treatment of cancer cells according to claim 1 wherein said human cancer cells comprise human breast cancer cells.

4. The method for treatment of cancer cells according to claim 1 wherein said fixed distance is 4-6 mm.

5. The method for treatment of cancer cells according to claim 1 wherein said fixed time is 40 seconds.

6. A method for treating cancer cells according to claim 1, wherein said step of applying electrical energy comprises applying electrical energy having a wavelength of 200-280 nm.

7. A method for treating cancer cells according to claim 1, wherein said media comprises saline.

8. The method for manufacturing plasma-activated media for treatment of cancer cells according to claim 1 wherein said self-organized pattern comprises a double ring.

9. A method for manufacturing plasma-activated media for treatment of cancer cells comprising:
   generating with an atmospheric discharge between an electrode and a surface of a liquid media to generate a plasma self-organized pattern at said surface of media, wherein the electrode is at a distance from the surface of the media and a plasma is formed in a gap between said electrode and said surface of said media; and
   maintaining said atmospheric discharge for a period of time greater than 10 seconds to generate reactive oxygen and nitrogen species.

10. The method for manufacturing plasma-activated media for treatment of cancer cells according to claim 9 wherein said distance between the electrode and the surface of the media is 4-6 mm.

11. The method for manufacturing plasma-activated media for treatment of cancer cells according to claim 9 wherein said self-organized pattern comprises a double ring.

12. The method for manufacturing plasma-activated media for treatment of cancer cells according to claim 9 wherein said media comprises saline solution.

* * * * *